(12) United States Patent
Alcaraz Asensio et al.

(10) Patent No.: US 9,097,715 B2
(45) Date of Patent: Aug. 4, 2015

(54) BLADDER CANCER DIAGNOSIS AND/OR PROGNOSIS METHOD

(75) Inventors: Antonio Alcaraz Asensio, Barcelona (ES); Lourdes Mengual Brichs, Barcelona (ES); Moises Burset Albareda, Barcelona (ES); Maria Jose Ribal Caparros, Barcelona (ES); Elisabet Ars Criach, Barcelona (ES)

(73) Assignee: FINA BIOTECH, S.L.U., Madrid (ES)

( * ) Notice: Subject to any disclaimer, the term of this patent is extended or adjusted under 35 U.S.C. 154(b) by 1289 days.

(21) Appl. No.: 12/532,139

(22) PCT Filed: Jun. 5, 2007

(86) PCT No.: PCT/ES2007/000330
§ 371 (c)(1),
(2), (4) Date: Dec. 18, 2009

(87) PCT Pub. No.: WO2008/113870
PCT Pub. Date: Sep. 25, 2008

(65) Prior Publication Data
US 2010/0086932 A1 Apr. 8, 2010

(30) Foreign Application Priority Data

Mar. 20, 2007 (ES) .................................. 200700727

(51) Int. Cl.
*C12Q 1/68* (2006.01)
*G01N 33/574* (2006.01)

(52) U.S. Cl.
CPC ........ *G01N 33/57407* (2013.01); *C12Q 1/6886* (2013.01); *C12Q 2600/118* (2013.01)

(58) Field of Classification Search
USPC ........................................................ 435/6.1
See application file for complete search history.

(56) References Cited

PUBLICATIONS

Kim et al.; Periostin is down-regulated in high grade human bladder cancers and suppresses in vitro cell invasiveness and in vivo metastasis of cancer cells; International Journal of Cancer; vol. 117, Issue 1, pp. 51-58; Oct. 20, 2005.*
HG U133 Plus 2.0 Array; Affymetrix Human Genome U133 Plus 2.0 Array; http://www.ncbi.nlm.nih.gov/geo/query/acc.cgi?acc=GPL570; publicly available Nov. 7, 2003.*
Menke et al.; Improved conditions for isolation and quantification of RNA in Urine specimens; Annals of the New York Academy of Sciences; vol. 1022, No. 1; pp. 185-189; published online Jan. 12, 2006.*
Adshead, J.M. et al., *Genetic initiation, progression and prognostic markers in transitional cell carcinoma of the bladder: a summary of the structural and transcriptional changes, and the role of developmental genes*, British Journal of Urology, 1998, vol. 82, pp. 503-512.
Babaian, R. et al., *Metastases from transitional cell carcinoma of urinary bladder*, Urology, Aug. 1980, vol. 16, Issue 2, pp. 142-144.
Bassi, P. et al., *Non-invasive diagnostic tests for bladder cancer: A review of the literature*, Urologia Internationalis, 2005, vol. 75, pp. 193-200.
Bastacky, S. et al., *The accuracy of urinary cytology in daily practice*, Cancer Cytopathology, American Cancer Society, Jun. 25, 1999, vol. 87, Issue 3, pp. 118-128.
Burch, J.D. et al., *Risk of bladder cancer by source and type of tobacco exposure: A case-control study*, Int. J. Cancer, Publication of the International Union Against Cancer, 1989, vol. 44, pp. 622-628.
Duggan, D. et al., *Expression profiling using cDNA microarrays*, Nature Genetics Supplement, Nature America Inc., Jan. 1999, vol. 21, pp. 10-14.
Dyrskjøt, L. et al., *Identifying distinct classes of bladder carcinoma using microarrays*, Nature Genetics, Nature Publishing Group, Jan. 2003, vol. 33, pp. 90-96.
Edwards, B. et al., *Annual report to the nation on the status of cancer, 1975-2002, featuring population-based trends in cancer treatment*, Journal of the National Cancer Institute, Oct. 5, 2005, vol. 97, Issue 19, pp. 1407-1427.
Eissa S. et al., *Comparison of cytokeratin 20 RNA and angiogenin in voided urine samples as diagnostic tools for bladder carcinoma*, Clinical Biochemistry, The Canadian Society of Clinical Chemists, 2004, vol. 37, pp. 803-810.
Elsamman, E. et al., *Differences in gene expression between noninvasive and invasive transitional cell carcinoma of the human bladder using complementary deoxyribonucleic acid microarray: Preliminary results*, Urologic Oncology: Seminars and Original Investigations, Elsevier Inc., 2006, vol. 24, pp. 109-115.
Fichera, E. et al., *A quantitative reverse transcription and polymerase chain reaction assay for human IFG-II allows direct comparison of IGF-II mRNA levels in cancerous breast, bladder, and prostate tissues*, Growth Hormone & IGF Research, Harcourt Publishers Ltd., 2000, vol. 10, pp. 61-70.
Granjeaud, S. et al., *Expression profiling: DNA arrays in many guises*, BioEssays, John Wiley & Sons, Inc., 1999, vol. 21, pp. 781-790.
Halling, K. et al., *A comparison of BTA stat, hemoglobin dipstick, telomerase and VYSIS urovysion assays for the detection of urothelial carcinoma in urine*, The Journal of Urology, American Urological Association, Inc., May 2002, vol. 167, pp. 2001-2006.
Jemal, A. et al., *Cancer Statistics, 2002*, CA Cancer J Clin, 2002, vol. 52, pp. 23-47.
Jones, J. Stephen, *DNA-based molecular cytology for bladder cancer surveillance*, Urology, Elsevier Inc., 2006, vol. 67 (Suppl 3A), pp. 35-47.
Knowles, M.A., *What we could do now: molecular pathology of bladder cancer*, Journal of Clinical Pathology: Molecular Pathology, 2001, vol. 54, pp. 215-221.

(Continued)

*Primary Examiner* — Jim Ketter
*Assistant Examiner* — Antonio Galisteo Gonzalez
(74) *Attorney, Agent, or Firm* — Knobbe, Martens, Olson & Bear, LLP

(57) ABSTRACT

A high sensitive and specific non-invasive bladder cancer diagnosis and/or prognosis method based on the detection and quantification of the gene expression of a combination of bladder tumor markers in bladder fluids is provided. A preferred combination of the markers consists of the combination of ANXA10, C14orf78, CTSE, CRH, IGF2, KLF9, KRT20, MAGEA3, POSTN, PPP1R14D, SLC1A6, TERT, ASAM and MCM10 genes.

4 Claims, 43 Drawing Sheets

(56) References Cited

PUBLICATIONS

Larsson, P.C.M. et al., *Allelic deletion fingerprinting of urine cell sediments in bladder cancer*, Molecular Diagnosis, Churchill Livingstone, Sep. 2001, vol. 6, Issue 3, pp. 181-188.

Lokeshwar, V. et al., *Bladder tumor markers beyond cytology: International consensus panel on bladder tumor markers*, Urology, Elsevier Inc., 2005, vol. 66 (Suppl 6A), pp. 35-63.

Mengual, L. et al., *Partially degraded RNA from bladder washing is a suitable sample for studying gene expression profiles in bladder cancer*, European Urology, European Association of Urology, Elsevier B.V., 2006, vol. 50, pp. 1347-1356.

Ohnishi, S. et al., *Downregulation and growth inhibitory effect of epithelial-type Krüppel-like transcription factor KLF4, but not KLF5, in bladder cancer*, Biochemical and Biophysical Research Communications, Elsevier Inc., 2003, vol. 308, pp. 251-256.

Olsburgh, J. et al., *Uroplakin gene expression in normal human tissues and locally advanced bladder cancer*, Journal of Pathology, John Wiley & Sons, Ltd., 2003, vol. 199, pp. 41-49.

Parekattil, S. et al., *Neural network using combined urine nuclear matrix protein-22, monocyte chemoattractant protein-1 and urinary intercellular adhesion molecule-1 to detect bladder cancer*, The Journal of Urology, American Urological Association, Mar. 2003, vol. 169, pp. 917-920.

Pisani, P. et al., *Estimates of the worldwide mortality from 25 cancers in 1990*, Int. J. Cancer, 1999, vol. 83, pp. 18-29.

Ramaswamy, S. et al., *Multiclass cancer diagnosis using tumor gene expression signatures*, PNAS, Dec. 18, 2001, vol. 98, Issue 26, pp. 15149-15154.

Sanchez-Carbayo, M. et al., *Molecular profiling of bladder cancer using cDNA microarrays: Defining histogenesis and biological phenotypes*, Cancer Research, Dec. 1, 2002, vol. 62, pp. 6973-6980.

Sanchez-Carbayo, M. et al., *Gene discovery in bladder cancer progression using cDNA microarrays*, American Journal of Pathology, Aug. 2003, vol. 163, Issue 2, pp. 505-516.

Sanchez-Carbayo, M. et al., *Tumor suppressor role of KiSS-1 in bladder cancer: Loss of KiSS-1 expression is associated with bladder cancer progression and clinical outcome*, American Journal of Pathology, American Society for Investigative Pathology, Feb. 2003, vol. 162, Issue 2, pp. 609-617.

Schmetter, B.S. et al., *A multicenter trial evaluation of the fibrin/fibrinogen degradation products test for detection and monitoring of bladder cancer*, The Journal of Urology, Sep. 1997, vol. 158, pp. 801-805.

Simoneau, M. et al., *Four tumor suppressor loci on chromosome 9q in bladder cancer: evidence for two novel candidate regions at 9q22.3 and 9q31*, Oncogene, 1999, vol. 18, pp. 157-163.

Soloway, M. et al., *Use of a new tumor marker, urinary NMP22, in the detection of occult or rapidly recurring transitional cell carcinoma of the urinary tract following surgical treatment*, The Journal of Urology, American Urological Association, Inc., Aug. 1996, vol. 156, pp. 363-367.

Takahashi, C. et al., *Detection of telomerase activity in prostate cancer by needle biopsy*, European Urology, 1997, vol. 32, pp. 494-498.

Takihana, Y. et al., *Real-time quantitative analysis for human telomerase reverse transcriptase mRNA and human telomerase RNA component mRNA expressions as markers for clinicopathologic parameters in urinary bladder cancer*, International Journal of Urology, 2006, vol. 13, pp. 401-408.

Trott, P. et al., *Comparison of bladder washings and urine cytology in the diagnosis of bladder cancer*, The Journal of Urology, The Williams & Wilkins Co., Dec. 1973, vol. 110, pp. 664-666.

Wiener, H.G. et al., *Can urine bound diagnostic tests replace cystoscopy in the management of bladder cancer?*, The Journal of Urology, American Urological Association, Inc., Jun. 1998, vol. 159, pp. 1876-1880.

Zeegers, M.P.A., et al., *The association between smoking, beverage consumption, diet and bladder cancer: a systematic literature review*, World Journal of Urology, Springer-Verlag, 2004, vol. 21, pp. 392-401.

\* cited by examiner

|  |  | Pools | | | Individual samples | | | | |
|---|---|---|---|---|---|---|---|---|---|
|  | No. | µarrays | qRT-PCR | Mean | 1 | 2 | 3 | 4 | 5 |
| TCN1 | 1 | 6,55 | 8,82 | 8,01 | 1,23 | -0,29 | 6,99 | 8,12 | 9,78 |
|  | 2 | 6,71 | 9,42 | 8,15 | 6,80 | 7,47 | -0,59 | 3,97 | 10,12 |
|  | 3 | 5,10 | 8,34 | 6,48 | 7,50 | 6,73 | 5,89 | 5,28 | 5,93 |
| SORBS1 | 1 |  |  |  |  |  |  |  |  |
|  | 2 |  |  |  |  |  |  |  |  |
|  | 3 |  |  |  |  |  |  |  |  |
| MYH11 | 1 | -6,03 | -7,60 | -6,70 | -11,53 | -9,47 | -6,03 | -9,57 | -5,06 |
|  | 2 | -3,52 | -4,40 | -4,11 | -6,89 | -2,19 | -9,32 | -8,71 | --- |
|  | 3 | -6,93 | -7,69 | -8,36 | -7,99 | -9,95 | -7,59 | -8,91 | --- |
| SRPX | 1 |  |  |  |  |  |  |  |  |
|  | 2 |  |  |  |  |  |  |  |  |
|  | 3 |  |  |  |  |  |  |  |  |
| CRH | 1 | 3,53 | 5,44 | 3,68 | -5,82 | 0,11 | -2,12 | 5,36 | 4,44 |
|  | 2 | 7,25 | 10,56 | 7,95 | 3,18 | 8,67 | 9,14 | 2,64 | --- |
|  | 3 | 6,11 | 8,22 | 5,95 | 7,83 | 4,29 | -2,12 | -1,71 | --- |
| KRT14 | 1 |  |  |  |  |  |  |  |  |
|  | 2 |  |  |  |  |  |  |  |  |
|  | 3 |  |  |  |  |  |  |  |  |
| RRM2 | 1 | 5,47 | 4,97 | 3,81 | 1,83 | 4,27 | 3,16 | 4,91 | 3,09 |
|  | 2 | 6,02 | 5,41 | 4,38 | 4,04 | 4,95 | 3,16 | 3,65 | 5,13 |
|  | 3 | 4,98 | 4,46 | 3,68 | 4,01 | 4,44 | 2,46 | 2,97 | 3,67 |
| FOSB | 1 |  |  |  |  |  |  |  |  |
|  | 2 |  |  |  |  |  |  |  |  |
|  | 3 |  |  |  |  |  |  |  |  |
| CEACAM6 | 1 | 6,42 | 8,02 | 8,23 | 4,50 | 2,21 | 10,53 | -0,19 | -0,17 |
|  | 2 | 3,00 | 4,72 | 4,29 | 6,34 | 3,92 | -2,81 | 0,40 | -0,87 |
|  | 3 | 6,35 | 8,04 | 8,17 | 4,13 | 7,83 | 10,13 | 5,85 | 3,62 |
| CES1 | 1 |  |  |  |  |  |  |  |  |
|  | 2 |  |  |  |  |  |  |  |  |
|  | 3 |  |  |  |  |  |  |  |  |

FIG. 5

| Gene Symbol | Affymetrix Clone | TaqMan Gene Expression Assay | RefSeq Gene Bank mRNA | Gene name |
|---|---|---|---|---|
| ABCA8 | 204719_at | Hs00200350_m1 | NM_007168 | ATP-binding cassette sub-family A ABC1 member 8. |
| ABL1 | 209765_at | Hs00245445_m1 | 2 RefSeqs | V-abl Abelson murine leukemia viral oncogene homolog 1. |
| ADAM19 | 222162_s_at | Hs00224960_m1 | 2 RefSeqs | A disintegrin and metalloproteinase domain 19 meltrin beta. |
| ADAMTS1 | 201792_at | Hs00199608_m1 | NM_006988 | A disintegrin-like and metalloprotease reprolysin type with thrombospondin type 1 motif 1. |
| AEBP1 | 206513_at | Hs00371239_m1 | NM_001129 | AE binding protein 1. |
| AIM2 | 206561_s_at | Hs00175457_m1 | NM_004833 | Absent in melanoma 2. |
| AKR1B10 | 228554_at | Hs00252524_m1 | NM_020299 | Aldo-keto reductase family 1 member B10 aldose reductase. |
| AL137566 | 202920_at | Hs00612017_s1 | AL137566 | |
| ANK2 | 222608_s_at | Hs00153998_m1 | NM_0186685 | Ankyrin 2 neuronal. |
| ANLN | 233011_at | Hs00218803_m1 | NM_000700 | Anillin actin binding protein scraps homolog Drosophila. |
| ANXA1 | 210143_at | Hs00167549_m1 | NM_007193 | Annexin A1. |
| ANXA10 | 204894_s_at | Hs00200464_m1 | NM_003734 | Annexin A10. |
| AOC3 | 206632_s_at | Hs00186647_m1 | NM_004900 | Amine oxidase copper containing 3 vascular adhesion protein 1. |
| APOBEC3B | 205239_at | Hs00358981_m1 | NM_001657 | Apolipoprotein B mRNA editing enzyme catalytic polypeptide-like 3B. |
| AREG | 225728_at | Hs00155832_m1 | NM_021069 | Amphiregulin schwannoma-derived growth factor. |
| ARGBP2 | 226834_at | Hs00221428_m1 | NM_024769 | Abl-interacting protein ArgBP2. |
| ASAM | 219918_s_at | Hs00293345_m1 | NM_018136 | Adipocyte-specific adhesion molecule. |
| ASPM | | Hs00411505_m1 | | Asp abnormal spindle-like microcephaly associated Drosophila. |

FIG. 8A

| Gene | Probe ID | Accession | Description |
|---|---|---|---|
| ATF3 | 202672_s_at | Hs00231069_m1 | activating transcription factor 3. |
| ATP5B | | Hs00266077_m1 | NM_001686 | |
| ATP8B2 | 226771_at | Hs00393111_m1 | NM_020452 | ATPase Class I type 8B member 2. |
| C2orf32 | 226751_at | Hs00384403_m1 | NM_015463 | DKFZP566K1924. Cromosome 2 open reading frame 32. |
| OLFML1 | 217525_at | Hs00416948_m1 | NM_198474 | MVAL564 UNQ564. Olfactomedin like-1 OLFML1 |
| BAG2 | 209406_at | Hs00188716_m1 | NM_004282 | Apoptosis regulator Bcl-2 protein. |
| MGC16635 | 236285_at | Hs00536653_s1 | NM_138433 | Hypothetical protein BC009980. LOC113730. Kelch repeat. |
| LOC387882 | 225105_at | Hs00329098_m1 | NM_207376 | |
| BMP5 | 205431_s_at | Hs00234930_m1 | NM_021073 | Bone morphogenetic protein 5. |
| KLF9 | 203542_s_at | Hs00230918_m1 | NM_001206 | Basic transcription element binding protein 1. |
| BUB1B | 203755_at | Hs00176169_m1 | NM_001211 | BUB1 budding uninhibited by benzimidazoles 1 homolog beta yeast. |
| C10orf3 | 218542_at | Hs00216688_m1 | NM_0181 | Chromosome 10 open reading frame 3. |
| C10orf87 | 1552566_at | Hs00332436_m1 | NM_144587 | Chromosome 10 open reading frame 87. |
| C14orf78 | 212992_at | Hs00746838_s1 | | Chromosome 14 open reading frame 78. |
| C2orf23 | 204364_s_at | Hs00224761_m1 | NM_022912 | Chromosome 2 open reading frame 23. TB2/DP1 and HVA22 related protein. |
| C6orf109 | 218883_s_at | Hs00209864_m1 | NM_015388 | KSHV latent nuclear antigen interacting protein 1. KLIP1. |
| C7 | 202992_at | Hs00175109_m1 | NM_000587 | Complement component 7. |
| CA2 | 209301_at | Hs00163869_m1 | NM_000067 | Carbonic anhydrase II. |
| CALD1 | 205525_at | Hs00189021_m1 | | Caldesmon 1. |
| CAPNS2 | 223832_s_at | Hs00260517_s1 | NM_032330 | Calpain small subunit 2. |

FIG. 8B

| | | | |
|---|---|---|---|
| CAV1 | 212097_at | Hs00184697_m1 | NM_001753 | Caveolin 1 caveolae protein 22kDa. |
| CBFA2T1 | 228827_at | Hs00231702_m1 | 4 RefSeqs | Core-binding factor runt domain alpha subunit 2; translocated to 1; cyclin D-related. |
| CCL11 | 210133_at | Hs00237013_m1 | NM_002986 | Chemokine C-C motif ligand 11. |
| CCL18 | 209924_at | Hs00268113_m1 | NM_002988 | Chemokine C-C motif ligand 18 pulmonary and activation-regulated. |
| CCL2 | 216598_s_at | Hs00234140_m1 | NM_002982 | Chemokine C-C motif ligand 2. |
| CCNA2 | 203418_at | Hs00153138_m1 | NM_001237 | Cyclin A2. |
| CCNB1 | 214710_s_at | Hs00259126_m1 | NM_031966 | Cyclin B1. |
| CCNB2 | 202705_at | Hs00270424_m1 | NM_004701 | cyclin B2. |
| CCND1 | | Hs00277039_m1 | NM_053056 | cyclin D1 PRAD1: parathyroid adenomatosis 1. |
| CCND2 | 200953_s_at | Hs00277041_m1 | NM_001759 | Cyclin D2. Regulation of cell cycle. Cytokinesis. |
| CCNE1 | | Hs00233356_m1 | 2 RefSeqs | Cyclin E1. |
| CDC2 | 210559_s_at | Hs00364293_m1 | NM_001786 | Cell division cycle 2 G1 to S and G2 to M. |
| CDC20 | 202870_s_at | Hs00415851_g1 | NM_001255 | CDC20 cell division cycle 20 homolog S. cerevisiae. |
| CDC6 | 203967_at | Hs00154374_m1 | NM_001254 | CDC6 cell division cycle 6 homolog S. cerevisiae. |
| CDCA1 | 223381_at | Hs00230097_m1 | 2 RefSeqs | Cell division cycle associated 1. |
| CDCA3 | 223307_at | Hs00229905_m1 | NM_031299 | Cell division cycle associated 3. |
| CDH1 | | Hs00170423_m1 | NM_004360 | Cadherin 1 type 1 E-cadherin epithelial. |
| CDH11 | 207173_x_at | Hs00156438_m1 | 2 RefSeqs | Cadherin 11 type 2 OB-cadherin osteoblast. |
| CDH19 | 206898_at | Hs00253534_m1 | NM_021153 | Cadherin 19 type 2. |
| CDKN2A | | Hs00233365_m1 | 3 RefSeqs | Cyclin-dependent kinase inhibitor 2A melanoma p16 inhibits CDK4. |
| CDKN2B | 236313_at | Hs00365249_m1 | NM_078487 | Cyclin-dependent kinase inhibitor 2B p15 inhibits CDK4. |

FIG. 8C

| | | | |
|---|---|---|---|
| CDKN3 | 209714_s_at | Hs00193192_m1 | NM_005192 | Cyclin-dependent kinase inhibitor 3 CDK2-associated dual specificity phosphatase. |
| CEACAM6 | 211657_at | Hs00366002_m1 | NM_002483 | Carcinoembryonic antigen-related cell adhesion molecule 6 non-specific cross reacting antigen. |
| CEACAM7 | 206199_at | Hs00185152_m1 | NM_006890 | Carcinoembryonic antigen-related cell adhesion molecule 7. |
| CENPA | 204962_s_at | Hs00156455_m1 | NM_001809 | Centromere protein A 17kDa. |
| CENPF | 207828_s_at | Hs00193201_m1 | NM_016343 | Centromere protein F 350/400ka mitosin. |
| CFL2 | 224663_s_at | Hs00368395_g1 | | cofilin 2 muscle. |
| ChGn | 219049_at | Hs00218054_m1 | NM_018371 | Chondroitin beta1 4 N-acetylgalactosaminyltransferase. |
| CHI3L1 | 209395_at | Hs00609691_m1 | NM_001276 | Chitinase 3-like 1 cartilage glycoprotein-39. |
| CKS2 | 204170_s_at | Hs00854958_g1 | NM_001827 | CDC28 protein kinase regulatory subunit 2. |
| CLCA2 | 206165_s_at | Hs00197957_m1 | NM_006536 | Chloride channel calcium activated family member 2. |
| CLCN3 | 201733_at | Hs00156527_m1 | NM_001829 | Chloride channel 3. |
| CLIC3 | 219529_at | Hs00362166_g1 | NM_004669 | Chloride intracellular channel 3. |
| CLIC4 | 201560_at | Hs00749895_s1 | NM_013943 | Chloride intracellular channel 4. |
| COL14A1 | 212865_s_at | Hs00385388_m1 | | Collagen type XIV alpha 1 undulin. |
| COL15A1 | 203477_at | Hs00266332_m1 | NM_001855 | Collagen type XV alpha 1. |
| COL1A2 | 202403_s_at | Hs00164099_m1 | NM_000089 | Collagen type I alpha 2. |
| COL3A1 | 215076_s_at | Hs00164103_m1 | NM_000090 | Collagen type III alpha 1 Ehlers-Danlos syndrome type IV autosomal dominant. |
| COL5A2 | 221730_at | Hs00169768_m1 | NM_000393 | Collagen type V alpha 2. Cell growth and/or maintenance. |
| COL6A1 | 213428_s_at | Hs00242448_m1 | NM_001848 | Collagen type VI alpha 1. Cell adhesion. |
| COL6A2 | 209156_s_at | Hs00242484_m1 | NM_001849 | Collagen type VI alpha 2. Cell-cell adhesion. |

FIG. 8D

| | | | |
|---|---|---|---|
| COLEC12 | 221019_s_at | Hs00560477_m1 | 2 RefSeqs | Collectin sub-family member 12. |
| CPA3 | 205624_at | Hs00157019_m1 | NM_001870 | Carboxypeptidase A3 mast cell. |
| CPE | 201116_s_at | Hs00175676_m1 | NM_001873 | Carboxypeptidase E. |
| CRH | 205630_at | Hs00174941_m1 | NM_000756 | Corticotropin releasing hormone. |
| CRTAC1 | 221204_s_at | Hs00216208_m1 | NM_018058 | Cartilage acidic protein 1. |
| CTGF | 209101_at | Hs00170014_m1 | NM_001901 | Connective tissue growth factor. |
| CTSE | 205927_s_at | Hs00157213_m1 | | cathepsin E. |
| CTTN | | Hs00193322_m1 | 2 RefSeqs | Cortactin. |
| VSIG2 | 228232_s_at | Hs00204823_m1 | NM_014312 | Cortical thymocyte receptor X. laevis CTX like. |
| CUGBP2 | 202157_s_at | Hs00272516_m1 | NM_006561 | CUG triplet repeat RNA binding protein 2. |
| CXCL12 | 209687_at | Hs00171022_m1 | | Chemokine C-X-C motif ligand 12 stromal cell-derived factor 1. |
| CXCR4 | 217028_at | Hs00237052_m1 | NM_003467 | Chemokine C-X-C motif receptor 4. |
| CYBRD1 | 222453_at | Hs00227411_m1 | NM_024843 | Cytochrome b reductase 1. Electron transport. |
| CYP24A1 | | Hs00167999_m1 | NM_000782 | Cytochrome P450 family 24 subfamily A polypeptide 1. |
| CYR61 | 201289_at | Hs00155479_m1 | NM_001554 | Cysteine-rich angiogenic inducer 61. Regulation of cell growth. |
| D4S234E | 209569_x_at | Hs00205189_m1 | NM_014392 | DNA segment on chromosome 4 unique 234 expressed sequence. |
| DBC1 | | Hs00180893_m1 | NM_014618 | Deleted in bladder cancer 1. |
| DCN | 209335_at | Hs00266491_m1 | | Decorin. Organogenesis. |
| DF | 205382_s_at | Hs00157263_m1 | NM_001928 | D component of complement adipsin. |
| DKFZp434B044 | 221541_at | Hs00230322_m1 | NM_031476 | hypothetical protein DKFZp434B044. |

FIG. 8E

| | | | |
|---|---|---|---|
| DKFZp564O0823 | 225809_at | Hs00209875_m1 | NM_015393 | DKFZP564O0823 protein |
| DKFZp586H2123 | 213661_at | Hs00405837_m1 | NM_015430 | DKFZP586H2123 protein. |
| DKK1 | 204602_at | Hs00183740_m1 | NM_012242 | Dickkopf homolog 1 Xenopus laevis. |
| DLG7 | 203764_at | Hs00207323_m1 | NM_014750 | Discs large homolog 7 Drosophila. |
| DOC1 | 1554966_a_at | Hs00706279_s1 | | Downregulated in ovarian cancer 1. |
| DPT | 213068_at | Hs00170030_m1 | NM_001937 | dermatopontin. Cell adhesion. |
| DPYSL3 | 201431_s_at | Hs00181665_m1 | NM_001387 | Dihydropyrimidinase-like 3. |
| DSCR1L1 | 203498_at | Hs00195165_m1 | NM_005822 | Down syndrome critical region gene 1-like 1. |
| DTR | 203821_at | Hs00181813_m1 | NM_001945 | Diphtheria toxin receptor heparin-binding epidermal growth factor-like growth factor. |
| DUSP1 | 201041_s_at | Hs00610256_g1 | NM_004417 | Dual specificity phosphatase 1. |
| E2F3 | | Hs00605457_m1 | NM_001949 | E2F transcription factor 3. |
| EBF | 227646_at | Hs00395513_m1 | NM_024007 | Early B-cell factor. |
| ECRG4 | 223623_at | Hs00260897_m1 | NM_032411 | Esophageal cancer related gene 4 protein. |
| ECT2 | 219787_s_at | Hs00216455_m1 | NM_018098 | Epithelial cell transforming sequence 2 oncogene. |
| EDNRA | 204464_s_at | Hs00609865_m1 | NM_001957 | Endothelin receptor type A. |
| EGR1 | 201694_s_at | Hs00152928_m1 | NM_001964 | early growth response 1. |
| ENTPD3 | 206191_at | Hs00154325_m1 | NM_001248 | Ectonucleoside triphosphate diphosphohydrolase 3. |
| EPHA3 | 206070_s_at | Hs00178327_m1 | NM_005233 | EphA3. |
| EPHA7 | 229288_at | Hs00177891_m1 | NM_004440 | EphA7. |
| ERBB2 | | Hs00170433_m1 | 2 RefSeqs | V-erb-b2 erythroblastic leukemia viral oncogene homolog 2 neuro/glioblastoma derived oncogene homolog avian. |

FIG. 8F

| | | | |
|---|---|---|---|
| F3 | 204363_at | Hs00175225_m1 | NM_001993 | Coagulation factor III thromboplastin tissue factor. |
| FABP4 | 203980_at | Hs00609791_m1 | NM_001442 | Fatty acid binding protein 4 adipocyte. |
| FABP6 | 210445_at | Hs00155029_m1 | NM_001445 | Fatty acid binding protein 6 ileal gastrotropin. |
| FAP | 209955_s_at | Hs00189476_m1 | NM_004460 | Fibroblast activation protein alpha. |
| FBLN1 | 202994_s_at | Hs00242545_m1 | 4 RefSeqs | Fibulin 1. |
| FBLN5 | 203088_at | Hs00197064_m1 | NM_006329 | Fibulin 5. |
| FBN1 | 202766_s_at | Hs00171191_m1 | NM_000138 | Fibrillin 1 Marfan syndrome. |
| FBN2 | 203184_at | Hs00417208_m1 | NM_001999 | Fibrillin 2 congenital contractural arachnodactyly. |
| FBXO32 | 225328_at | Hs00369714_m1 | | F-box only protein 32. |
| FEN1 | 204768_s_at | Hs00748727_s1 | NM_004111 | Flap structure-specific endonuclease 1. |
| FGF3 | | Hs00173742_m1 | NM_005247 | Fibroblast growth factor 3 murine mammary tumor virus integration site v-int-2 oncogene homolog. |
| FGFR1 | | Hs00241111_m1 | 9 RefSeqs | Fibroblast growth factor receptor 1 fms-related tyrosine kinase 2 Pfeiffer syndrome. |
| FGFR3 | 204380_s_at | Hs00179829_m1 | 2 RefSeqs | Fibroblast growth factor receptor 3 achondroplasia thanatophoric dwarfism. |
| FGL2 | 227265_at | Hs00173847_m1 | NM_006682 | |
| FLJ10159 | 218974_at | Hs00215979_m1 | NM_018013 | Hypothetical protein FLJ10159 |
| FLJ10719 | 213007_at | Hs00289551_m1 | NM_018193 | Hipothetycal protein FLJ10719 |
| FLJ11029 | 228273_at | Hs00383634_m1 | NM_018304 | Hypothetical protein FLJ11029 |
| FLJ13710 | 222835_at | Hs00388227_m1 | NM_024817 | Hypothetical protein FLJ13710. |
| TSC | 218872_at | Hs00215487_m1 | NM_017899 | Hipothetycal protein FLJ20607 |
| FLJ20701 | 219093_at | Hs00374054_g1 | | Hypothetical protein FLJ20701 |

FIG. 8G

| | | | |
|---|---|---|---|
| FLJ21986 | 228728_at | Hs00227735_m1 | NM_024913 | Hypothetical protein FLJ21986 |
| FLJ23191 | 219747_at | Hs00375503_m1 | NM_024574 | Hypothetical protein FLJ23191 |
| SPOCD1 | 235417_at | Hs00375905_m1 | NM_144569 | Hipothetycal protein FLJ2234.Transcription elongation factor S-II central region. |
| FLJ31052 | 238452_at | Hs00708284_s1 | NM_152378 | Hypothetical protein FLJ31052 |
| FLJ32569 | 239929_at | Hs00611179_m1 | NM_152491 | Proteolysis and peptidolysis. |
| FLJ38736 | 227174_at | Hs00419054_m1 | NM_182758 | Hypothetical protein FLJ38736. |
| FN1 | 211719_x_at | Hs00365058_m1 | 7 RefSeqs | Fibronectin 1. |
| FNBP1 | 212288_at | Hs00390705_m1 | NM_015033 | Formin binding protein 1. |
| FOS | 209189_at | Hs00170630_m1 | NM_005252 | V-fos FBJ murine osteosarcoma viral oncogene homolog. |
| FOSB | 202768_at | Hs00171851_m1 | NM_006732 | FBJ murine osteosarcoma viral oncogene homolog B. |
| FOXF1 | 205935_at | Hs00230962_m1 | NM_001451 | Forkhead box F1. |
| FOXM1 | 202580_x_at | Hs00153543_m1 | 2 RefSeqs | Forkhead box M1. |
| FYN | 210105_s_at | Hs00176628_m1 | 3 RefSeqs | FYN oncogene related to SRC FGR YES. |
| FZD7 | 203706_s_at | Hs00275833_s1 | NM_003507 | Frizzled homolog 7 Drosophila. |
| GATA6 | 210002_at | Hs00232018_m1 | NM_005257 | GATA binding protein 6. |
| GEM | 204472_at | Hs00170633_m1 | NM_005261 | GTP binding protein overexpressed in skeletal muscle. |
| GGH | 203560_at | Hs00608257_m1 | NM_003878 | Gamma-glutamyl hydrolase conjugase folylpolygammaglutamyl hydrolase. |
| GHR | 205498_at | Hs00174872_m1 | NM_000163 | Growth hormone receptor. |
| GJB2 | 223278_at | Hs00269615_s1 | NM_004004 | Gap junction protein beta 2 26kDa connexin 26. Cell-cell signaling. |
| GJB6 | 231771_at | Hs00272726_s1 | NM_006783 | Gap junction protein beta 6 connexin 30. |

FIG. 8H

| | | | |
|---|---|---|---|
| GKN1 | 220191_at | Hs00219734_m1 | NM_019617 | Gastrokine 1. |
| GMNN | 218350_s_at | Hs00210707_m1 | NM_015895 | Geminin DNA replication inhibitor. |
| GPC6 | 227059_at | Hs00170677_m1 | NM_005708 | Glypican 6. Cell growth and/or maintenance. |
| GPM6B | 209167_at | Hs00383529_m1 | 4 RefSeqs | Glycoprotein M6B. |
| GPR124 | 221814_at | Hs00262150_m1 | NM_032777 | G protein-coupled receptor 124. |
| GREM1 | 218469_at | Hs00171951_m1 | NM_013372 | Gremlin 1 homolog cysteine knot superfamily Xenopus laevis. |
| GSN | | Hs00609276_m1 | 2 RefSeqs | Gelsolin amyloidosis Finnish type. |
| GULP1 | 204235_s_at | Hs00169604_m1 | NM_016315 | GULP engulfment adaptor PTB domain containing 1. |
| GUSB | | Hs99999908_m1 | NM_000181 | |
| H19 | 224646_x_at | Hs00399294_g1 | | H19 imprinted maternally expressed untranslated mRNA. |
| HEPH | 203903_s_at | Hs00207710_m1 | NM_000186 | Hephaestin. |
| CFH | 213800_at | Hs00164830_m1 | | H factor 1 complement. |
| HIST1H1C | 209398_at | Hs00271185_s1 | NM_005319 | Histone 1 H1c. |
| HIST1H2BD | 209911_x_at | Hs00371070_m1 | NM_138720 | Histone 1 H2bd. |
| HIST1H2BG | 210387_at | Hs00374317_s1 | NM_003518 | Histone 1 H2bg. |
| HIST2H2AA | 214290_s_at | Hs00358508_s1 | NM_003516 | Histone 2 H2aa. |
| HIST2H2BE | 202708_s_at | Hs00269023_s1 | NM_003528 | Histone 2 H2be. |
| HMGB2 | 208808_s_at | Hs00357789_g1 | NM_002129 | High-mobility group box 2. |
| HMOX1 | 203665_at | Hs00157965_m1 | NM_002133 | Heme oxygenase decycling 1. |
| HN1 | 217755_at | Hs00602957_m1 | 3 RefSeqs | Hematological and neurological expressed 1. |

FIG. 8I

| | | | | |
|---|---|---|---|---|
| HOP | 211597_s_at | Hs00261238_m1 | 3 RefSeqs | Homeodomain-only protein. |
| HOXB6 | 205366_s_at | Hs00255831_s1 | 3 RefSeqs | Homeo box B6. |
| HOXD4 | 205522_at | Hs00429605_m1 | NM_014621 | Homeo box D4. |
| HPRT | | Hs99999909_m1 | NM_000194 | |
| HRAS | | Hs00610483_m1 | NM_005343 | |
| HSPC150 | 223229_at | Hs00204359_m1 | NM_014176 | HSPC150 protein similar to ubiquitin-conjugating enzyme. |
| HSPCB | | Hs00607336_gH | NM_007355 | |
| HTR1F | | Hs00265296_s1 | NM_000866 | 5-hydroxytryptamine serotonin receptor 1F. |
| IER3 | 201631_s_at | Hs00174674_m1 | NM_003897 | Immediate early response 3. |
| IGF1 | 209541_at | Hs00153126_m1 | NM_000618 | Insulin-like growth factor 1 somatomedin C. |
| IGF2 | 210881_s_at | Hs00171254_m1 | NM_000612 | Insulin-like growth factor 2 somatomedin A. |
| IGFBP3 | 210095_s_at | Hs00181211_m1 | NM_000598 | Insulin-like growth factor binding protein 3. |
| IGFBP5 | 211959_at | Hs00181213_m1 | NM_000599 | Insulin-like growth factor binding protein 5. |
| IGHM | 216491_x_at | Hs00378512_m1 | | Immunoglobulin heavy constant mu. |
| IL6 | 205207_at | Hs00174131_m1 | NM_000600 | Interleukin 6 interferon beta 2. |
| INA | 204465_s_at | Hs00190771_m1 | NM_032727 | Internexin neuronal intermediate filament protein alpha. |
| INHBA | 210511_s_at | Hs00170103_m1 | NM_002192 | Inhibin beta A activin A activin AB alpha polypeptide. |
| IQGAP3 | 229490_s_at | Hs00603642_m1 | NM_178229 | IQ motif containing GTPase activating protein 3. Ras GTPase-activating protein. |
| ITGA8 | AA903473 | | NM_003638 | |
| ITM2A | 202746_at | Hs00191609_m1 | NM_004867 | Integral membrane protein 2A. |

FIG. 8J

| | | | |
|---|---|---|---|
| JAM2 | 229127_at | Hs00221894_m1 | NM_021219 | Junctional adhesion molecule 2. |
| JAM3 | 212813_at | Hs00230289_m1 | NM_032801 | Junctional adhesion molecule 3. |
| JUNB | 215595_at | Hs00357891_s1 | NM_002229 | Jun B proto-oncogene. |
| KCNG1 | 214595_at | Hs00158410_m1 | NM_002237 | Potassium voltage-gated channel subfamily G member 1. |
| KDELR3 | 204017_at | Hs00423556_m1 | 2 RefSeqs | KDEL Lys-Asp-Glu-Leu endoplasmic reticulum protein retention receptor 3. |
| KIAA0101 | 202503_s_at | Hs00207134_m1 | NM_014736 | KIAA0101 gene product |
| KIAA0186 | 206102_at | Hs00221421_m1 | NM_021067 | KIAA0186 gene product. |
| KIAA0992 | 200897_s_at | Hs00363101_m1 | NM_016081 | Palladin. |
| KIF11 | 204444_at | Hs00189698_m1 | NM_004523 | Kinesin family member 11. |
| KIF14 | 206364_at | Hs00208408_m1 | NM_014875 | Kinesin family member 14. |
| KIF20A | 218755_at | Hs00194882_m1 | NM_005733 | Kinesin family member 20A. |
| KIF2C | 209408_at | Hs00199232_m1 | NM_006845 | Kinesin family member 2C. |
| KIF4A | 218355_at | Hs00602211_g1 | NM_012310 | Kinesin family member 4A. |
| KISS1 | 220239_at | Hs00158486_m1 | NM_002256 | KiSS-1 metastasis-suppressor. |
| KLHL7 | 201088_at | Hs00375239_m1 | NM_018846 | Kelch-like 7 Drosophila. |
| KPNA2 | 209351_at | Hs00818252_g1 | NM_002266 | Karyopherin alpha 2 RAG cohort 1 importin alpha 1. |
| KRT14 | 213953_at | Hs00265033_m1 | NM_000526 | Keratin 14 epidermolysis bullosa simplex Dowling-Meara Koebner. |
| KRT20 | 209016_s_at | Hs00300643_m1 | NM_019010 | Keratin 20. |
| KRT7 | 227198_at | Hs00818825_m1 | NM_005556 | Keratin 7. |
| LAF4 | | Hs00171448_m1 | NM_002285 | Lymphoid nuclear protein related to AF4. |

FIG. 8K

| | | | | |
|---|---|---|---|---|
| LEPR | 209894_at | Hs00174497_m1 | NM_002303 | Leptin receptor. |
| LGALS1 | 201105_at | Hs00169327_m1 | NM_002305 | Lectin galactoside-binding soluble 1 galectin 1. |
| LIFR | 225575_at | Hs00158730_m1 | NM_002310 | Leukemia inhibitory factor receptor. |
| LOC83468 | 227070_at | Hs00229917_m1 | NM_031302 | Gycosyltransferase. |
| LOX | 215446_s_at | Hs00184700_m1 | NM_002317 | Lysyl oxidase |
| LPPR4 | 213496_at | Hs00322721_m1 | NM_014839 | Plasticity related gene 1. |
| LUM | 229554_at | Hs00158940_m1 | NM_002345 | Lumican. |
| LY6D | 206276_at | Hs00170353_m1 | NM_003695 | Lymphocyte antigen 6 complex locus D. |
| MAD2L1 | 203362_s_at | Hs00829154_g1 | NM_002358 | MAD2 mitotic arrest deficient-like 1 yeast. |
| MAGEA3 | 209942_x_at | Hs00366532_m1 | NM_005362 | Melanoma antigen family A 3. |
| MAGEA9 | 210437_at | Hs00245619_s1 | NM_005365 | Melanoma antigen family A 9. |
| MAMDC2 | 228885_at | Hs00299196_m1 | NM_153267 | MAM domain containing 2. |
| MAN1C1 | 214180_at | Hs00220595_m1 | NM_020379 | Mannosidase alpha class 1C member 1. |
| MAP1B | 226084_at | Hs00195487_m1 | 2 RefSeqs | Microtubule-associated protein 1B. |
| MCM10 | 220651_s_at | Hs00218560_m1 | 2 RefSeqs | Minichromosome maintenance deficient 10 S. |
| MCM2 | 202107_s_at | Hs00170472_m1 | NM_004526 | MCM2 minichromosome maintenance deficient 2 mitotin S. |
| MDM2 | | Hs00242813_m1 | 3 RefSeqs | Mdm2 transformed 3T3 cell double minute 2 p53 binding protein mouse. |
| MELK | 204825_at | Hs00207681_m1 | NM_014791 | Maternal embryonic leucine zipper kinase. |
| MFAP2 | 203417_at | Hs00250064_m1 | 2 RefSeqs | Microfibrillar-associated protein 2. |
| MFAP4 | 212713_at | Hs00412974_m1 | NM_002404 | Microfibrillar-associated protein 4. |

FIG. 8L

| Gene | Probe | Accession | Description |
|---|---|---|---|
| TUBB6 | 209191_at | Hs00603164_m1 | NM_032525 | Tubulin beta MGC4083. |
| MGC45780 | 229839_at | Hs00382351_m1 | NM_173833 | Hypothetical protein. |
| MGC57827 | 225834_at | Hs00822131_m1 | NM_207418 | Similar to RIKEN cDNA 2700049P18 gene. |
| MGP | 202291_s_at | Hs00179899_m1 | NM_000900 | Matrix Gla protein. |
| MKI67 | 212021_s_at | Hs00606991_m1 | NM_002417 | Antigen identified by monoclonal antibody Ki-67. |
| MMD | 203414_at | Hs00202450_m1 | NM_012329 | Monocyte to macrophage differentiation-associated. |
| MMP1 | 204475_at | Hs00233958_m1 | NM_002421 | Matrix metalloproteinase 1 interstitial collagenase. |
| MMP12 | 204580_at | Hs00159178_m1 | NM_002426 | Matrix metalloproteinase 12 macrophage elastase. |
| MRS2L | 218538_s_at | Hs00252895_m1 | NM_020662 | MRS2-like magnesium homeostasis factor S. cerevisiae. |
| MRVI1 | 226047_at | Hs00180652_m1 | | Murine retrovirus integration site 1 homolog. |
| MSRB3 | 225782_at | Hs00827017_m1 | NM_198080 | Methionine sulfoxide reductase B3 |
| MST1R | 205455_at | Hs00234013_m1 | NM_002447 | Macrophage stimulating 1 receptor c-met-related tyrosine kinase. |
| MTHFD2 | 201761_at | Hs00759197_s1 | NM_006636 | Methylene tetrahydrofolate dehydrogenase NAD+ dependent methenyltetrahydrofolate cyclohydrolase. |
| MUC7 | | Hs00379529_m1 | NM_152291 | Mucin 7 salivary. |
| MYADM | 225673_at | Hs00414763_m1 | NM_138373 | Myeloid-associated differentiation marker |
| MYBPC1 | 214087_s_at | Hs00159451_m1 | | Myosin binding protein C slow type. |
| MYC | | Hs00153408_m1 | NM_002467 | V-myc myelocytomatosis viral oncogene homolog avian. |
| NEK2 | 204641_at | Hs00601227_mH | NM_002497 | NIMA never in mitosis gene a-related kinase 2. |
| NEXN | 1552309_a_at | Hs00332124_m1 | NM_144573 | Nexilin F actin binding protein. |
| NFIA | 226806_s_at | Hs00325656_m1 | NM_005595 | |

FIG. 8M

| | | | |
|---|---|---|---|
| NFIB | 213029_at | Hs00232149_m1 | NM_005596 | Nuclear factor I/B. |
| NFIL3 | 203574_at | Hs00356605_g1 | NM_005384 | Nuclear factor interleukin 3 regulated. |
| FLJ22595 | 220468_at | Hs00540047_s1 | NM_025047 | Hipothetycal protein FLJ22595 |
| NMES1 | 223484_at | Hs00260902_m1 | NM_006169 | Normal mucosa of esophagus specific 1. Nucleus. |
| NNMT | 202237_at | Hs00196287_m1 | NM_006169 | Nicotinamide N-methyltransferase. |
| NOPE | 227870_at | Hs00326335_m1 | NM_020962 | Likely ortholog of mouse neighbor of Punc E11. |
| NQO1 | 201468_s_at | Hs00168547_m1 | NM_000903 | NADPH dehydrogenase quinone 1. |
| NR2F1 | 209505_at | Hs00818842_m1 | NM_005654 | Nuclear receptor subfamily 2 group F member 1. |
| NR4A1 | 202340_x_at | Hs00172437_m1 | NM_173157 | Nuclear receptor subfamily 4 group A member 1. |
| NR4A2 | 204621_s_at | Hs00428691_m1 | 4 RefSeqs | Nuclear receptor subfamily 4 group A member 2. |
| NR4A3 | 209959_at | Hs00175077_m1 | | Nuclear receptor subfamily 4 group A member 3. |
| NTNG2 | 218039_at | Hs00287286_m1 | NM_032536 | Netrin G2. |
| NUSAP1 | 218039_at | Hs00153533_m1 | NM_016359 | Nucleolar and spindle associated protein 1. |
| OAS1 | 202869_at | Hs00242943_m1 | 2 RefSeqs | 2' 5'-oligoadenylate synthetase 1 40/46kDa. |
| OLFML3 | 218162_at | Hs00220180_m1 | NM_020190 | Olfactomedin-like 3. |
| OSR2 | 213568_at | Hs00369588_m1 | NM_053001 | Odd-skipped-related 2A protein. |
| PDGFC | | Hs00211916_m1 | NM_016205 | |
| PDGFRA | 203131_at | Hs00183486_m1 | NM_006206 | Platelet-derived growth factor receptor alpha polypeptide. |
| PDLIM3 | 209621_s_at | Hs00205533_m1 | NM_014476 | PDZ and LIM domain 3. |
| PDZRN3 | 212915_at | Hs00392900_m1 | | PDZ domain containing RING finger 3. |

FIG. 8N

| | | | |
|---|---|---|---|
| PEG10 | 212094_at | Hs00248288_s1 | NM_015068 | Paternally expressed 10. |
| PFKFB3 | 202464_s_at | Hs00190079_m1 | NM_004566 | 6-phosphofructo-2-kinase/fructose-2 6-biphosphatase 3. |
| Pfs2 | 221521_s_at | Hs00211479_m1 | NM_016095 | DNA replication complex GINS protein PSF2. DNA replication. |
| PGM5 | 226303_at | Hs00222671_m1 | NM_021965 | phosphoglucomutase 5. Cell-cell adherens junction. |
| PLA2G2A | 203649_s_at | Hs00179898_m1 | NM_000300 | Phospholipase A2 group IIA platelets synovial fluid. Lipid catabolism. |
| PLAGL1 | 208318_x_at | Hs00243030_m1 | NM_002656 | Pleiomorphic adenoma gene-like 1. |
| PLCB4 | 203895_at | Hs00168656_m1 | | Phospholipase C beta 4. |
| PLEKHC1 | 209209_s_at | Hs00235033_m1 | NM_006832 | Pleckstrin homology domain containing family C with FERM domain member 1. |
| PLN | 204939_s_at | Hs00160179_m1 | NM_002667 | phospholamban. |
| PLSCR4 | 218901_at | Hs00220482_m1 | NM_020353 | Phospholipid scramblase 4. |
| PMP22 | 210139_s_at | Hs00165556_m1 | | Peripheral myelin protein 22. |
| POLQ | 219510_at | Hs00198196_m1 | 2 RefSeqs | Polymerase DNA directed theta. |
| POSTN | 1555778_a_at | Hs00170815_m1 | NM_006475 | Periostin osteoblast specific factor. |
| POU1F1 | | Hs00230821_m1 | NM_000306 | POU domain class 1 transcription factor 1 Pit1 growth hormone factor 1. |
| PPIA o CYC | | Hs99999904_m1 | 3 RefSeqs | |
| PPP1R12B | 201957_at | Hs00364078_m1 | | Protein phosphatase 1 regulatory inhibitor subunit 12B. |
| PPP1R14D | 220082_at | Hs00214613_m1 | NM_017726 | Protein phosphatase 1 regulatory inhibitor subunit 14D. |
| PRC1 | 218009_s_at | Hs00187740_m1 | | Protein regulator of cytokinesis 1. |
| PRKAR2B | 203680_at | Hs00176966_m1 | NM_002736 | Protein kinase cAMP-dependent regulatory type II beta. |
| PRL | | Hs00168730_m1 | NM_000948 | Prolactin. |

FIG. 80

| | | | |
|---|---|---|---|
| PSAT1 | 223062_s_at | Hs00795278_mH | 2 RefSeqs | Phosphoserine aminotransferase 1. |
| PTCH | | Hs00181117_m1 | NM_000264 | Patched homolog Drosophila. |
| PTEN | | Hs00829813_s1 | NM_000314 | Phosphatase and tensin homolog mutated in multiple advanced cancers 1. |
| PTGS2 | 1554997_a_at | Hs00153133_m1 | NM_000963 | Prostaglandin-endoperoxide synthase 2 prostaglandin G/H synthase and cyclooxygenase. |
| PTN | 211737_x_at | Hs00383235_m1 | NM_002825 | Pleiotrophin heparin binding growth factor 8 neurite growth-promoting factor 1. |
| PTPRC | | Hs00236304_m1 | 3 RefSeqs | |
| PTRF | 1557938_s_at | Hs00396859_m1 | NM_012232 | Polymerase I and transcript release factor abans AL545542. |
| RAB23 | 229504_at | Hs00212407_m1 | | RAB23 member RAS oncogene family. |
| RACGAP1 | 222077_s_at | Hs00374747_m1 | NM_013277 | Rac GTPase activating protein 1. |
| RAI2 | 219440_at | Hs00253960_s1 | NM_021785 | Retinoic acid induced 2. |
| RAMP | 218585_s_at | Hs00212788_m1 | NM_016448 | RA-regulated nuclear matrix-associated protein. |
| RASL12 | 219167_at | Hs00275429_m1 | NM_016563 | RAS-like family 12. |
| RB1 | | Hs00153108_m1 | NM_000321 | Retinoblastoma 1 including osteosarcoma. |
| RBM24 | 235004_at | Hs00290607_m1 | NM_153020 | RNA binding motif protein 24. |
| RECK | 205407_at | Hs00221638_m1 | NM_021111 | Reversion-inducing-cysteine-rich protein with kazal motifs. |
| RFC3 | 204127_at | Hs00161357_m1 | 2 RefSeqs | Replication factor C activator 1 3 38kDa. DNA replication. |
| RGS1 | 216834_at | Hs00175260_m1 | NM_002922 | Regulator of G-protein signalling 1. Immune response. |
| RNASE4 | 213397_x_at | Hs00377763_m1 | | Ribonuclease RNase A family 4. |
| RODH | 205700_at | Hs00366258_m1 | NM_003725 | 3-hydroxysteroid epimerase. |

FIG. 8P

| | | | |
|---|---|---|---|
| RPESP | 235210_s_at | Hs00541931_m1 | NM_153225 | RPE-spondin. |
| RRM2 | 209773_s_at | Hs00357247_g1 | NM_001034 | Ribonucleotide reductase M2 polypeptide. |
| S100A10 | 238909_at | Hs00741221_m1 | NM_002966 | S100 calcium binding protein A10 annexin II ligand calpactin I light polypeptide p11. |
| SBLF | 213413_at | Hs00538997_m1 | | Stoned B-like factor. |
| SCN7A | 228504_at | Hs00161546_m1 | NM_002976 | Sodium channel voltage-gated type VII alpha. |
| SELL | 204563_at | Hs00174151_m1 | NM_000655 | Selectin L lymphocyte adhesion molecule 1. |
| SELM | 226051_at | Hs00369741_m1 | NM_080430 | Selenoprotein M. |
| SERPINB3 | 209719_x_at | Hs00199468_m1 | NM_006919 | Serine or cysteine proteinase inhibitor clade B ovalbumin member 3. |
| SETBP1 | 205933_at | Hs00210209_m1 | NM_015559 | SET binding protein 1. |
| SFRP1 | 202037_s_at | Hs00610060_m1 | NM_003012 | Secreted frizzled-related protein 1. |
| SLC1A6 | 1554593_s_at | Hs00192604_m1 | NM_005071 | Solute carrier family 1 high affinity aspartate/glutamate transporter member 6. |
| SLIT2 | 209897_s_at | Hs00191193_m1 | NM_004787 | slit homolog 2 (Drosophila). |
| SMAD6 | | Hs00178579_m1 | NM_005585 | SMAD mothers against DPP homolog 6 Drosophila. |
| SMOC2 | 223235_s_at | Hs00405777_m1 | NM_022138 | SPARC related modular calcium binding 2. |
| SNX10 | 218404_at | Hs00203362_m1 | NM_013322 | Sorting nexin 10. |
| SOCS3 | 227697_at | Hs00269575_s1 | NM_003955 | Suppressor of cytokine signaling 3. |
| SOX4 | 213668_s_at | Hs00268388_s1 | NM_003107 | SRY sex determining region Y-box 4. |
| SOX9 | 202935_s_at | Hs00165814_m1 | NM_000346 | SRY sex determining region Y-box 9 campomelic dysplasia autosomal sex-reversal |
| SPARCL1 | 200795_at | Hs00190740_m1 | NM_004684 | SPARC-like 1 mast9 hevin. |
| SPON1 | 209436_at | Hs00323883_m1 | | Spondin 1 extracellular matrix protein. |

FIG. 8Q

| Gene | Probe | Hs ID | NM ID | Description |
|---|---|---|---|---|
| SPP1 | 209875_s_at | Hs00167093_m1 | NM_000582 | Secreted phosphoprotein 1 osteopontin bone sialoprotein I early T-lymphocyte activation 1. |
| SPRR3 | 218990_s_at | Hs00271304_m1 | NM_005416 | Small proline-rich protein 3. Structural molecule activity. |
| SRPX | 204955_at | Hs00196867_m1 | NM_006307 | Sushi-repeat-containing protein X-linked. |
| STC1 | 230746_s_at | Hs00174970_m1 | NM_003155 | Stanniocalcin 1. |
| STK6 | 208079_s_at | Hs00269212_m1 | NM_003600 | Serine/threonine kinase 6. |
| STN2 | 235852_at | Hs00263833_m1 | NM_033104 | Stonin 2. |
| SULF1 | 212354_at | Hs00290918_m1 | NM_015170 | Sulfatase 1. |
| SULT1E1 | 219934_s_at | Hs00193690_m1 | NM_005420 | Sulfotransferase family 1E estrogen-preferring member 1. |
| TCF21 | 204931_at | Hs00162646_m1 | | Transcription factor 21. |
| TCF8 | 212764_at | Hs00611018_m1 | NM_030751 | Transcription factor 8 represses interleukin 2 expression. |
| TCN1 | 205513_at | Hs00169055_m1 | NM_001062 | transcobalamin I (vitamin B12 binding protein, R binder family). |
| TEAD2 | 226408_at | Hs00366217_m1 | NM_003598 | TEA domain family member 2. |
| TEGT | | Hs00162661_m1 | NM_003217 | |
| TERT | | Hs00162669_m1 | 2 RefSeqs | Telomerase reverse transcriptase. |
| TGFB1I1 | 209651_at | Hs00210887_m1 | NM_015927 | Transforming growth factor beta 1 induced transcript 1. |
| TIMP2 | 224560_at | Hs00234278_m1 | NM_003255 | Tissue inhibitor of metalloproteinase 2. |
| TK1 | 1554408_a_at | Hs00177406_m1 | NM_003258 | Thymidine kinase 1 soluble. |
| TMPO | 203432_at | Hs00162842_m1 | NM_003276 | Thymopoietin. DNA binding. |
| TNA | 205200_at | Hs00162844_m1 | NM_003278 | Tetranectin. |
| TNC | 201645_at | Hs00233648_m1 | NM_002160 | Tenascin C. |

FIG. 8R

| Gene | Probe | Accession | Description |
|---|---|---|---|
| TNRC9 | 216623_x_at | Hs00300355_m1 | | Trinucleotide repeat containing 9. |
| TOP2A | 201291_s_at | Hs00172214_m1 | NM_001067 | Topoisomerase DNA II alpha 170kDa. |
| TOPK | 219148_at | Hs00218544_m1 | NM_018492 | T-LAK cell-originated protein kinase. |
| TP53 | | Hs00153349_m1 | NM_000546 | Tumor protein p53 Li-Fraumeni syndrome. |
| TPX2 | 210052_s_at | Hs00201616_m1 | NM_012112 | TPX2 microtubule-associated protein homolog Xenopus laevis. |
| TRIP13 | 204033_at | Hs00188500_m1 | NM_004237 | Thyroid hormone receptor interactor 13. |
| TSPAN-2 | 227236_at | Hs00194836_m1 | NM_005725 | Tetraspan 2. Cell motility. |
| TTK | 204822_at | Hs00177412_m1 | NM_003318 | TTK protein kinase. |
| TU3A | 209074_s_at | Hs00200376_m1 | NM_007177 | TU3A protein. |
| TYMS | 202589_at | Hs00426591_m1 | NM_001071 | Thymidylate synthetase. |
| UBD | 205890_s_at | Hs00197374_m1 | NM_006398 | Ubiquitin D. |
| UBE2C | 202954_at | Hs00738962_m1 | NM_181799 | Ubiquitin-conjugating enzyme E2C. |
| UHRF1 | 225655_at | Hs00273589_m1 | NM_013282 | Ubiquitin-like containing PHD and RING finger domains 1. |
| URB | 225242_s_at | Hs00736722_m1 | | Steroid sensitive gene 1 |

FIG. 8S

| | | | |
|---|---|---|---|
| WFDC1 | 219478_at | Hs00221849_m1 | NM_021197 | WAP four-disulfide core domain 1. |
| WISP1 | 229802_at | Hs00365573_m1 | 2 RefSeqs | WNT1 inducible signaling pathway protein 1. |
| ZAK | 225665_at | Hs00370447_m1 | 2 RefSeqs | Sterile alpha motif and leucine zipper containing kinase AZK. |
| ZBTB16 | 228854_at | Hs00232313_m1 | NM_006006 | zinc finger and BTB domain containing 16 |
| ZFP36 | 201531_at | Hs00185658_m1 | NM_003407 | Zinc finger protein 36 C3H type homolog mouse. |
| ZNF217 | | Hs00232417_m1 | NM_006526 | Zinc finger protein 217. |
| ZWINT | 204026_s_at | Hs00199952_m1 | | ZW10 interactor. |
| ZYX | | Hs00170299_m1 | NM_003461 | Zyxin. Cell adhesion. |
| 18S | | Hs99999901_s1 | | Eukaryotic 18S rRNA |

FIG. 8T

| Gene Symbol | TaqMan Gene Expression Assay |
|---|---|
| ANK2 | Hs00153998_m1 |
| ANLN | Hs00218803_m1 |
| ANXA10 | Hs00200464_m1 |
| APOBEC3B | Hs00358981_m1 |
| ASAM | Hs00293345_m1 |
| ASPM | Hs00411505_m1 |
| BUB1B | Hs00176169_m1 |
| C10orf3 | Hs00216688_m1 |
| C14orf78 | Hs00746838_s1 |
| CCNA2 | Hs00153138_m1 |
| CCNB1 | Hs00259126_m1 |
| CDC2 | Hs00364293_m1 |
| CDC20 | Hs00415851_g1 |
| CDCA1 | Hs00230097_m1 |
| CDCA3 | Hs00229905_m1 |
| CDKN3 | Hs00193192_m1 |
| CENPA | Hs00156455_m1 |
| CENPF | Hs00193201_m1 |
| CFH | Hs00164830_m1 |
| ChGn | Hs00218054_m1 |
| COL1A2 | Hs00164099_m1 |
| CRH | Hs00174941_m1 |
| CTSE | Hs00157213_m1 |
| CYP24A1 | Hs00167999_m1 |

FIG. 9A

| | |
|---|---|
| DLG7 | Hs00207323_m1 |
| EBF | Hs00395513_m1 |
| F3 | Hs00175225_m1 |
| FABP6 | Hs00155029_m1 |
| FGFR3 | Hs00179829_m1 |
| FLJ11029 | Hs00383634_m1 |
| FLJ21986 | Hs00227735_m1 |
| FLJ31052 | Hs00708284_s1 |
| FN1 | Hs00365058_m1 |
| FOXM1 | Hs00153543_m1 |
| GJB2 | Hs00269615_s1 |
| GJB6 | Hs00272726_s1 |
| GUSB | Hs99999908_m1 |
| HPRT | Hs99999909_m1 |
| IGF2 | Hs00171254_m1 |
| INA | Hs00190771_m1 |
| IQGAP3 | Hs00603642_m1 |
| KIAA0101 | Hs00207134_m1 |
| KIAA0186 | Hs00221421_m1 |
| KIAA0992 | Hs00363101_m1 |
| KIF11 | Hs00189698_m1 |
| KIF20A | Hs00194882_m1 |
| KIF2C | Hs00199232_m1 |
| KIF4A | Hs00602211_g1 |

FIG. 9B

| Gene symbol | TaqMan Gene Expression Assay |
|---|---|
| KISS1 | Hs00158486_m1 |
| KLF9 | Hs00230918_m1 |
| KRT14 | Hs00265033_m1 |
| KRT20 | Hs00300643_m1 |
| KRT7 | Hs00818825_m1 |
| MAGEA3 | Hs00366532_m1 |
| MAGEA9 | Hs00245619_s1 |
| MAN1C1 | Hs00220595_m1 |
| MCM10 | Hs00218560_m1 |
| MELK | Hs00207681_m1 |
| MKI67 | Hs00606991_m1 |
| MMP1 | Hs00233958_m1 |
| MMP12 | Hs00159178_m1 |
| NEK2 | Hs00601227_mH |
| NFIA | Hs00325656_m1 |
| NQO1 | Hs00168547_m1 |
| NR2F1 | Hs00818842_m1 |
| PDGFC | Hs00211916_m1 |
| PDZRN3 | Hs00392900_m1 |
| PLAGL1 | Hs00243030_m1 |
| PLSCR4 | Hs00220482_m1 |
| POLQ | Hs00198196_m1 |
| POSTN | Hs00170815_m1 |

FIG. 9C

| | |
|---|---|
| PPIA o CYC | Hs99999904_m1 |
| PPP1R12B | Hs00364078_m1 |
| PPP1R14D | Hs00214613_m1 |
| PRC1 | Hs00187740_m1 |
| PRKAR2B | Hs00176966_m1 |
| PTPRC | Hs00236304_m1 |
| RAMP | Hs00212788_m1 |
| RNASE4 | Hs00377763_m1 |
| SBLF | Hs00538997_m1 |
| SERPINB3 | Hs00199468_m1 |
| SLC1A6 | Hs00192604_m1 |
| SPON1 | Hs00323883_m1 |
| SPP1 | Hs00167093_m1 |
| STN2 | Hs00263833_m1 |
| TERT | Hs00162669_m1 |
| TNRC9 | Hs00300355_m1 |
| TOP2A | Hs00172214_m1 |
| TOPK | Hs00218544_m1 |
| TPX2 | Hs00201616_m1 |
| TRIP13 | Hs00188500_m1 |
| TTK | Hs00177412_m1 |
| UHRF1 | Hs00273589_m1 |
| ZBTB16 | Hs00232313_m1 |
| ZWINT | Hs00199952_m1 |
| 18S | Hs99999901_s1 |

FIG. 9D

| Gene symbol | TaqMan Gene Expression Assay |
|---|---|
| ANLN | Hs00218803_m1 |
| ANXA10 | Hs00200464_m1 |
| ASAM | Hs00293345_m1 |
| ASPM | Hs00411505_m1 |
| C14orf78 | Hs00746838_s1 |
| CCNA2 | Hs00153138_m1 |
| CDC2 | Hs00364293_m1 |
| CDC20 | Hs00415851_g1 |
| CDCA1 | Hs00230097_m1 |
| CENPF | Hs00193201_m1 |
| CFH | Hs00164830_m1 |
| CRH | Hs00174941_m1 |
| CTSE | Hs00157213_m1 |
| CYP24A1 | Hs00167999_m1 |
| EBF | Hs00395513_m1 |
| FGFR3 | Hs00179829_m1 |
| FOXM1 | Hs00153543_m1 |
| GJB2 | Hs00269615_s1 |
| GUSB | Hs99999908_m1 |
| IGF2 | Hs00171254_m1 |
| IQGAP3 | Hs00603642_m1 |
| KIF20A | Hs00194882_m1 |
| KIF2C | Hs00199232_m1 |
| KIF4A | Hs00602211_g1 |
| KLF9 | Hs00230918_m1 |

FIG. 10A

| | |
|---|---|
| KRT14 | Hs00265033_m1 |
| KRT20 | Hs00300643_m1 |
| MAGEA3 | Hs00366532_m1 |
| MAGEA9 | Hs00245619_s1 |
| MCM10 | Hs00218560_m1 |
| MELK | Hs00207681_m1 |
| MMP1 | Hs00233958_m1 |
| MMP12 | Hs00159178_m1 |
| NEK2 | Hs00601227_mH |
| NR2F1 | Hs00818842_m1 |
| PDZRN3 | Hs00392900_m1 |
| POLQ | Hs00198196_m1 |
| POSTN | Hs00170815_m1 |
| PPIA | Hs99999904_m1 |
| PPP1R14D | Hs00214613_m1 |
| PTPRC | Hs00236304_m1 |
| SLC1A6 | Hs00192604_m1 |
| TERT | Hs00162669_m1 |
| TOP2A | Hs00172214_m1 |
| TPX2 | Hs00201616_m1 |
| TRIP13 | Hs00188500_m1 |
| 18S | Hs99999901_s1 |

FIG. 10B

BLADDER CANCER DIAGNOSIS AND/OR PROGNOSIS METHOD

This application is U.S. National Phase of International Application PCT/ES2007/000330, filed Jun. 5, 2007 designating the U.S., and published in a language other than English as WO 2008/113870 on Sep. 25, 2008, which claims priority to Spanish Patent Application No. P200700727, filed Mar. 20, 2007.

FIELD OF THE INVENTION

The field of application of the present invention is within the healthcare field, mainly in the "Oncological Urology" and "Molecular Biology" field. This invention is specifically aimed at bladder cancer diagnosis and prognosis methods.

BACKGROUND OF THE INVENTION

Bladder cancer, or vesical cancer, is the second most frequent tumor of the genitourinary tract after prostate cancer [Jemal A, Thomas A, Murray T, Thun M. *Cancer statistics, 2002. CA Cancer J Clin* 2002; 52:23-47]. In a global context, it represents approximately 3 and 1%, in men and women, respectively, of all the deaths due to cancer. In absolute values, this means that about 95,000 men and about 35,000 women die every year due to this pathology. The ratio between incidence and death is different depending on the degree of development of each country. As extreme examples, it could be mentioned that in the North America area this ratio would be close to 0.2, whereas in sub-Saharan regions it would increase up to 0.6 [Edwards B K, Brown M L, Wingo P A et al. *Annual report to the nation on the status of cancer, 1975-2002, featuring population-based trends in cancer treatment. J Natl Cancer Inst* 2005; 97:1407-27; Pisani P, Parkin D M, Bray F, Ferlay J. *Estimates of the worldwide mortality from 25 cancers in 1990. Int J Cancer* 1999; 83:18-29].

Unlike other tumors, familial genetic predisposition factors have virtually not been detected for the moment. In contrast, several environmental factors strongly related to bladder tumors have been detected. One of the most important factors, not only due to its relation to the disease but also due to its incidence in the population, is smoking. It has been observed that smokers have a risk three times higher than non-smokers of developing a bladder tumor. In fact, one third of bladder tumors are associated to tobacco consumption. Unfortunately, the carcinogenic agents present in tobacco have still not been clearly identified [Burch J D, Rohan T E, Howe G R et al. *Risk of bladder cancer by source and type of tobacco exposure: a case-control study. Int J Cancer* 1989; 44:622-28; Zeegers M P, Kellen E, Buntinx F, van den Brandt P A. *The association between smoking, beverage consumption, diet and bladder cancer: a systematic literature review. World J Urol* 2004; 21:392-401].

Different types of disorders can be found in the bladder at cell level. There are benign changes such as epithelial hyperplasias, urothelial metaplasias and Von Brunn's nests, among others. In contrast, dysplasias would correspond to disorders that are more or less intermediate between normal epithelium and carcinoma. Finally, different types of urothelial carcinomas are found in the bladder, which can divided into adenocarcinomas, squamous tumors and transitional cell carcinomas (TCC).

More than 90% of bladder tumors are TCCs. At the time of their diagnosis, approximately 75% are superficial tumors, 20% are invading muscular layers (infiltrating or invasive TCCs) and 5% are already metastatic. Of the superficial cases, approximately 20% are cured by means of a single surgical intervention, whereas between 50 and 70% recur one or more times after surgery, but never become infiltrating tumors. Between 10 and 30% of these superficial tumors become infiltrating tumors. These tumors are aggressive, poor-prognosis tumors with a mortality after 5 years of 50% and in the metastasized cases, the mortality after two years is 100% [Sanchez-Carbayo M, Socci N D, Charytonowicz E et al. *Molecular profiling of bladder cancer using cDNA microarrays: defining histogenesis and biological phenotypes. Cancer Res* 2002; 62:6973-80; Adshead J M, Kessling A M, Ogden C W. *Genetic initiation, progression and prognostic markers in transitional cell carcinoma of the bladder: a summary of the structural and transcriptional changes, and the role of developmental genes. Br J Urol* 1998; 82:503-12; Babaian R J, Johnson O F, Llamas L, Ayala A G. *Metastases from transitional cell carcinoma of urinary bladder. Urology* 1980; 16:142-44].

The genetic pathways of superficial and invasive TCCs, although related, seem to be quite different. The most usual progression in superficial tumors seems to be hyperplasia, atypia and finally low-grade papillary TCCs. In invasive tumors, it is most usual to progress from an atypia to a dysplasia, to then pass to a tumor in situ (Tis) and end in an infiltrating tumor [Knowles M A. *What we could do now: molecular pathology of bladder cancer. Mol Pathol* 2001; 54:215-21].

Current diagnosis systems are based on a combination of urinary cytology (from squamous cells in urine) and of the direct observation of the bladder by means of cystoscopy. The latter is actually the main diagnostic and follow-up technique for tumors. It is performed by transurethral route, therefore it is an invasive and rather unpleasant technique for the patients. The sensitivity and specificity of this technique were believed to be quite high, although improvements in the actual technique (fluorescence cystoscopy) indicate that this is probably not so and that part of the recurrence observed in superficial tumors could be due to the lack of total resection in non-visible parts thereof [Jones J S. *DNA-based molecular cytology for bladder cancer surveillance. Urology* 2006; 67:35-45]. Urinary cytology is in turn a non-invasive diagnostic technique with a high sensitivity and specificity for high-grade tumors. However, this technique shows limitations for detecting low-grade tumors [Bastacky S, Ibrahim S, Wilczynski S P, Murphy W M. *The accuracy of urinary cytology in daily practice. Cancer* 1999; 87:118-28]. Furthermore, the interpretation of the cytology is highly observer-dependent, therefore they may be inter-observer differences, especially in low-grade tumors.

All these limitations have led to the search for more reliable non-invasive bladder cancer markers. Finding a non-invasive marker with a high sensitivity and specificity for bladder TCC would be very helpful for clinical practice. In fact, several studies describe new tumor markers in urine, such as the test for the bladder tumor antigen NMP22 [Wiener H G, Mian C, Haitel A, Pycha A, Schatzl G, Marberger M. *Can urine bound diagnostic tests replace cystoscopy in the management of bladder cancer? J Urol* 1998; 159:1876-80; Soloway M S, Briggman V, Carpinito G A et al. *Use of a new tumor marker, urinary NMP22, in the detection of occult or rapidly recurring transitional cell carcinoma of the urinary tract following surgical treatment. J Urol* 1996; 156:363-67], fibrin degradation products [Schmetter B S, Habicht K K, Lamm D L et al. *A multicenter trial evaluation of the fibrin/fibrinogen degradation products test for detection and monitoring of bladder cancer. J Urol* 1997; 158:801-5.], telomerase [Takihana Y, Tsuchida T, Fukasawa M, Araki I, Tanabe N, Takeda M. *Real-time quantitative analysis for human telomerase reverse transcriptase mRNA and human telomerase RNA component mRNA expressions as markers for clinicopathologic parameters in urinary bladder cancer. Int J Urol* 2006; 13:401-8], tests based on fluorescent in situ hybridization [Hailing K C, King W, Sokolova I A et al. *A comparison of BTA stat, hemoglobin dipstick, telomerase and Vysis UroVysion assays for the detection of urothelial carcinoma in urine. J Urol* 2002; 167:2001-6] or flow cytometry [Takahashi C, Miyagawa I, Kumano S, Oshimura M. *Detection of telomerase activity in prostate cancer by needle biopsy. Eur Urol* 1997; 32:494-98; Trott P A, Edwards L. *Comparison of bladder washings and urine cytology in the diagnosis of bladder cancer. J Urol* 1973; 110:664-66], but although most of them have a higher sensitivity than urinary cytology, the latter is still the most specific [Bassi P, De M, V, De Lisa A et al. *Non-invasive diagnostic tests for bladder cancer: a review of the literature. Urol Int* 2005; 75:193-200].

It is known that many and very varied genetic disorders are found in urothelial tumors, therefore the current tendency is to search for genetic markers (either at the DNA, RNA or protein level) which can indicate the presence of carcinomas in the analyzed sample. Furthermore, it would be very interesting to be able to discriminate the aggressiveness of the tumor of a patient with these same markers, as this would allow a much more personalized and effective treatment. Finally, some of these markers could be possible therapeutic targets for developing new drugs to combat cancer.

Until recently, the capacity to analyze gene expression patterns was limited to a few genes per experiment. New technologies, such as DNA microarrays have completely changed the scenario. Thousands of genes can currently be analyzed in a single assay [Duggan D J, Bittner M, Chen Y, Meltzer P, Trent J M. *Expression profiling using cDNA microarrays. Nat Genet* 1999; 21:10-14; Granjeaud S, Bertucci F, Jordan B R. *Expression profiling: DNA arrays in many guises. Bioessays* 1999; 21:781-90]. Therefore, massive expression results of all tumor types have started to appear in literature, including bladder tumors [Sanchez-Carbayo M, Socci N D, Charytonowicz E et al. *Molecular profiling of bladder cancer using cDNA microarrays: defining histogenesis and biological phenotypes. Cancer Res* 2002; 62:6973-80; Ramaswamy S, Tamayo P, Rifkin R et al. *Multiclass cancer diagnosis using tumor gene expression signatures. Proc Natl Acad Sci USA* 2001.98:15149-54; Sanchez-Carbayo M, Socci N D, Lozano J J et al. *Gene discovery in bladder cancer progression using cDNA microarrays. Am J Pathol* 2003; 163:505-16; Sanchez-Carbayo M, Capodieci P, Cordon-Cardo C. *Tumor suppressor role of KiSS-1 in bladder cancer loss of KiSS-1 expression is associated with bladder cancer progression and clinical outcome. Am J Pathol* 2003; 162:609-17; Dyrskjot L, Thykjaer T, Kruhoffer M et al. *Identifying distinct classes of bladder carcinoma using microarrays. Nat Genet* 2003; 33:90-96], although most of the results have not been made public in their entirety. However, up until now, the studies which have been conducted with specific bladder cancer markers have been focused on one or on very few genes [Olsburgh J, Hamden P, Weeks R et al. *Uroplakin gene expression in normal human tissues and locally advanced bladder cancer. J Pathol* 2003; 199:41-49; Fichera E, Liang S, Xu Z, Guo N, Mineo R, Fujita-Yamaguchi Y. *A quantitative reverse transcription and polymerase chain reaction assay for human IGF-II allows direct comparison of IGF-II mRNA levels in cancerous breast, bladder, and prostate tissues. Growth Horm IGF Res* 2000; 10:61-70; Simoneau M, Aboulkassim T O, LaRue H, Rousseau F, Fradet Y. *Four tumor suppressor loci on chromosome 9q in bladder cancer: evidence for two novel candidate regions at 9q22.3 and 9q31. Oncogene* 1999; 18:157-63].

Given that the nature of these tumors is very heterogeneous, it does not seem very likely to be able to identify all or most carcinomas with a single marker. Thus, to be able to characterize most tumors it seems to be essential to combine several of the best markers to some type of extent.

In addition, although the direct analysis of urothelial tissue is the most comfortable alternative for developing a routine diagnostic method, it would be very interesting, as has been mentioned above, that said method were not invasive, because the latter decrease the quality of life of the patients and represent a much higher economic burden for healthcare.

Bladder fluids (urine or bladder washing) which are in contact with the entire bladder epithelium, and therefore with the tumor mass, seem to be a good alternative for detecting tumor markers, given that they represent an easy and non-invasive way to obtain the sample to be analyzed. Thus, a large number of works have been focused on the study of tumor markers in urine in the search for a non-invasive diagnostic method for bladder TCC. In fact, different tests with this objective have been marketed (NMP22, UroVysion, ImmunoCyt, Accu-Dx, etc.).

One alternative, which has still not been marketed, is the detection of bladder TCC in urine samples by means of determining the gene expression of bladder cancer markers. In fact, there are some studies suggesting the usefulness of this methodology, although they have been conducted with one or a few marker genes [Parekattil S J, Fisher H A, Kogan B A. *Neural network using combined urine nuclear matrix protein-22, monocyte chemoattractant protein-1 and urinary intercellular adhesion molecule-1 to detect bladder cancer. J Urol* 2003; 169:917-20; Eissa S, Kenawy G, Swellam M, El Fadle A A, Abd El-Aal A A, El Ahmady O. *Comparison of cytokeratin 20 RNA and angiogenin in voided urine samples as diagnostic tools for bladder carcinoma. Clin Biochem* 2004; 37:803-10; Larsson P C, Beheshti B, Sampson H A, Jewett M A, Shipman R. *Allelic deletion fingerprinting of urine cell sediments in bladder cancer. Mol Diagn* 2001; 6:181-88].

In response to these needs, the inventors, after an important research work, have identified 14 bladder tumor marker genes, from which they have developed a bladder cancer diagnosis and prognosis method based on the detection and quantification of the gene expression of these genes by means of quantitative real-time PCR in RNA extracted from bladder fluids, and their subsequent computer combination by means of an "alarm system".

BRIEF DESCRIPTION OF THE DRAWINGS

FIG. 5: Results of quantitative real-time PCR (qRT-PCR) of the pools and the individual samples contained therein. The table is divided into pools (left part) and into individual samples (right). The columns of the pools indicate the pool number (No.), the expression levels observed in the microarrays (µarrays) and the levels quantified by means of qRT-PCR (qRT-PCR). The first column of the individual samples corresponds to the arithmetic mean of the expressions of the individual samples contained in the pool (mean), which are indicated in the following columns (1-5). Each row corresponds to a gene (TCN1, SORBS1, MYH11, SRPX, CRH, KRT14, RRM2, FOSB, CEACAM6, CES1), with the different expression levels for each pool.

FIG. 7.A and T, tumor samples; FIG. 7.B). The nomenclature of the samples follows the following rules: if the sample starts with the letter "B", it refers to a tumor bladder fluid sample; if it starts by "CB", it refers to a control bladder fluid sample; if the initial "R" appears after the sample number, it refers to a bladder washing sample; if on the other hand, the initial "O" appears, it refers to a urine sample.

FIG. 8 (A-T): List of 384 diagnostic, prognostic and endogenous control genes for bladder cancer. This list has been obtained from the analysis by means of Affymetrix microarrays of pools of bladder tumor tissue samples with different stages and tumor grades and control bladder mucosa samples.

FIG. 9 (A-D): List of 96 diagnostic, prognostic and endogenous control genes for bladder cancer. This list has been obtained by means of the analysis of 60 bladder fluid samples in microfluidic cards containing the 384 genes of FIG. 8. The gene symbol and the name of the TaqMan Gene Expression Assay selected for the TaqMan Low Density Array microfluidic card are indicated.

FIGS. 10 (A and B): List of 48 diagnostic, prognostic and endogenous control genes for bladder cancer. This list has been obtained by means of the analysis of 140 bladder fluid samples in microfluidic cards containing the 96 genes of FIG. 9. The gene symbol and the name of the TaqMan Gene Expression Assay selected for the TaqMan Low Density Array microfluidic card are indicated.

OBJECT OF THE INVENTION

Figure 1A:
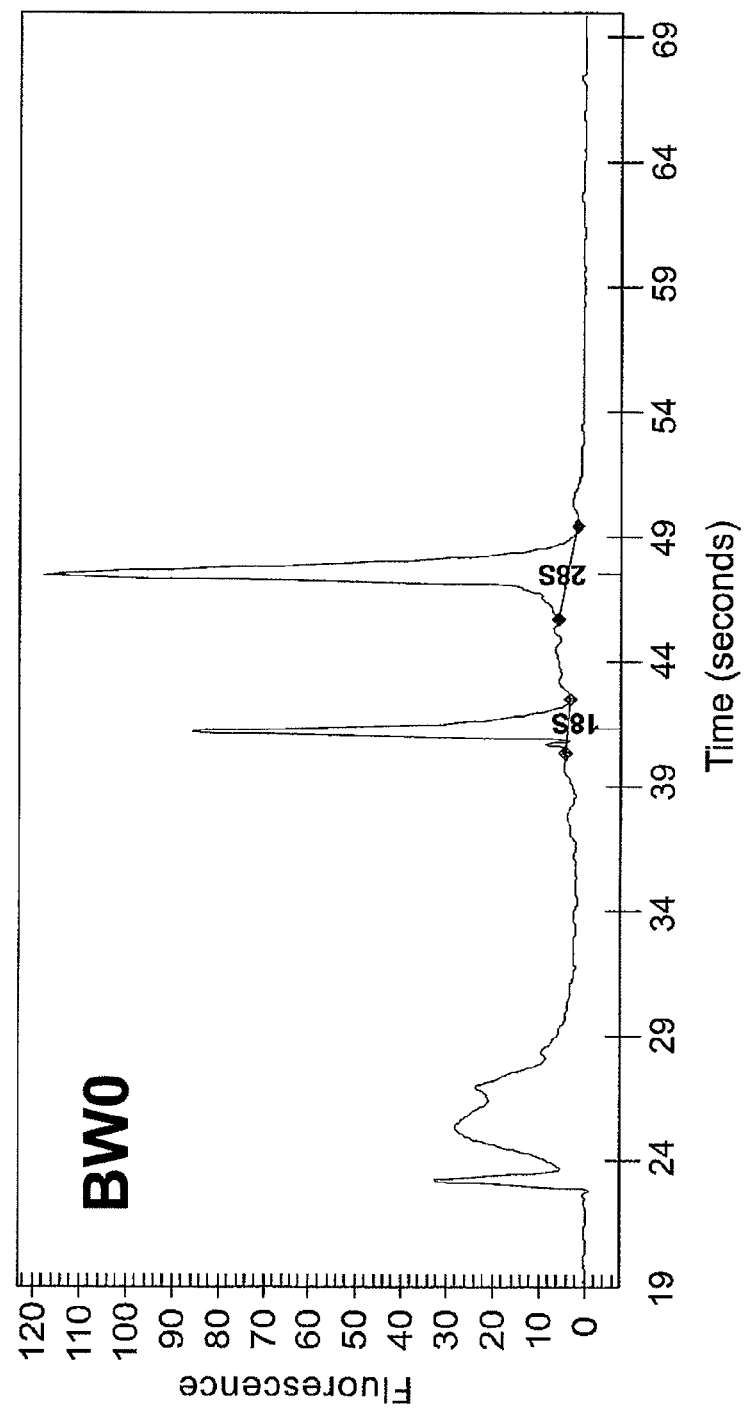
FIG. 1 (A-J): Electropherograms obtained with the Agilent 2100 Bioanalyzer of the samples of intact RNA (BW0) (FIG. 1.A) and partially degraded RNA (BW1, BW2, BW3) (FIGS. 1.B, 1.C, 1.D) of bladder washing, bladder tumor (T0, T1, T2, T3) (FIGS. 1.E, 1.F, 1.G, 1.H) and pool of control samples (C) (FIG. 1.I) and gel with the bands of the ribosomal RNAs (28S and 18S) of each of the analyzed samples (FIG. 1.J). The numbers 0, 1, 2 and 3 are assigned to the samples in increasing order of degradation and for the samples with RNA of a comparable quality.
Figure 1B:
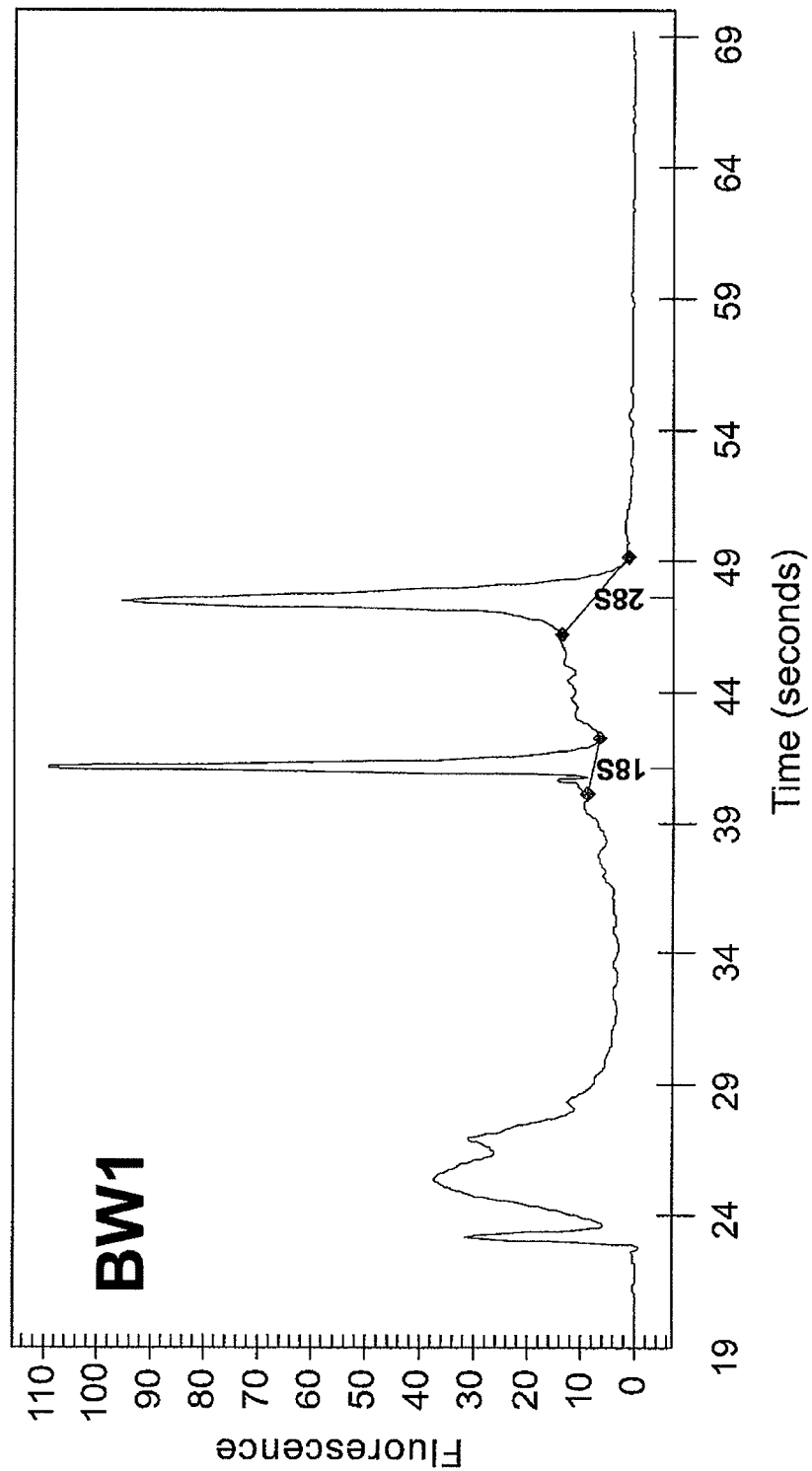
Figure 1C:
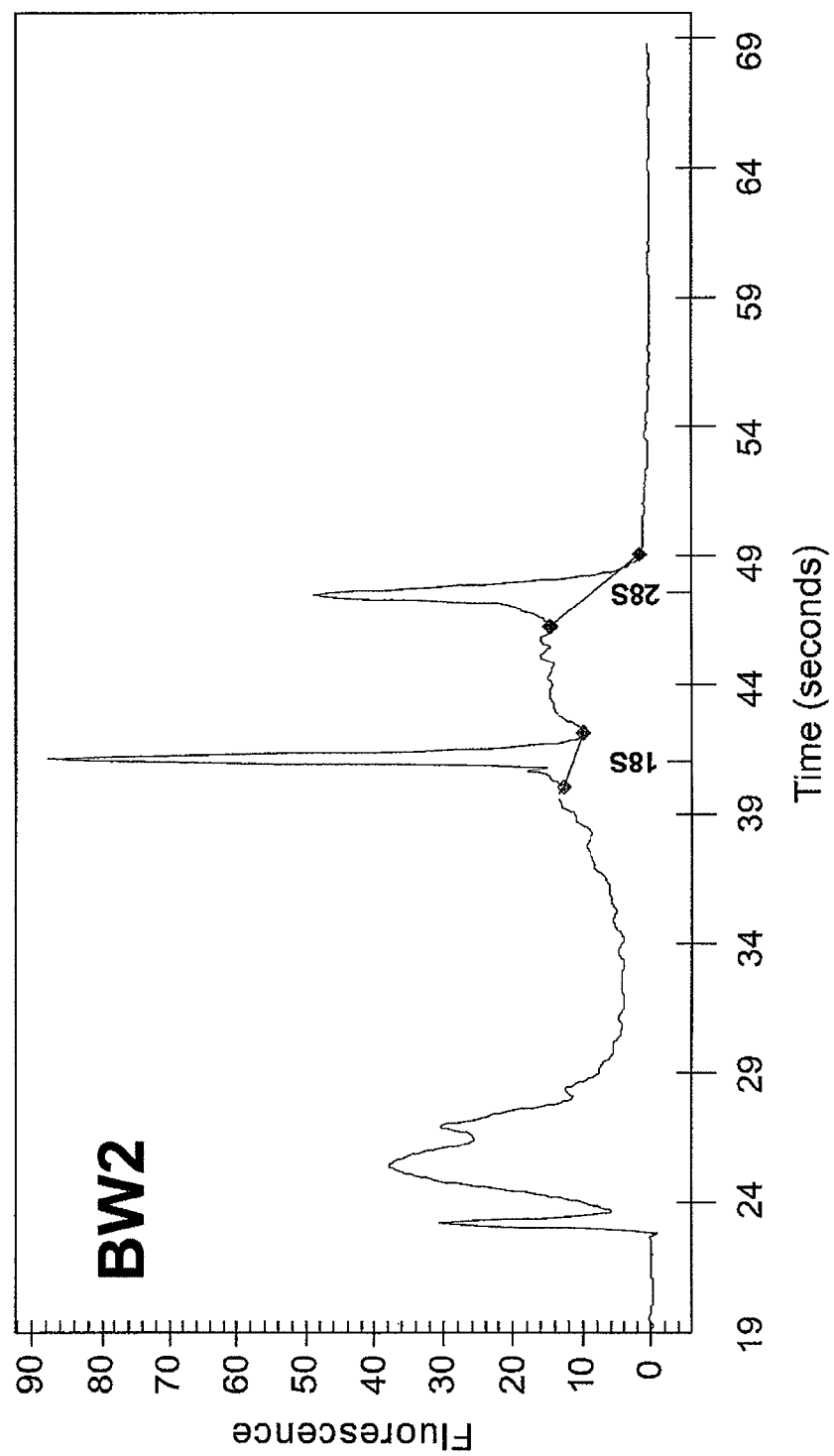
Figure 1D:
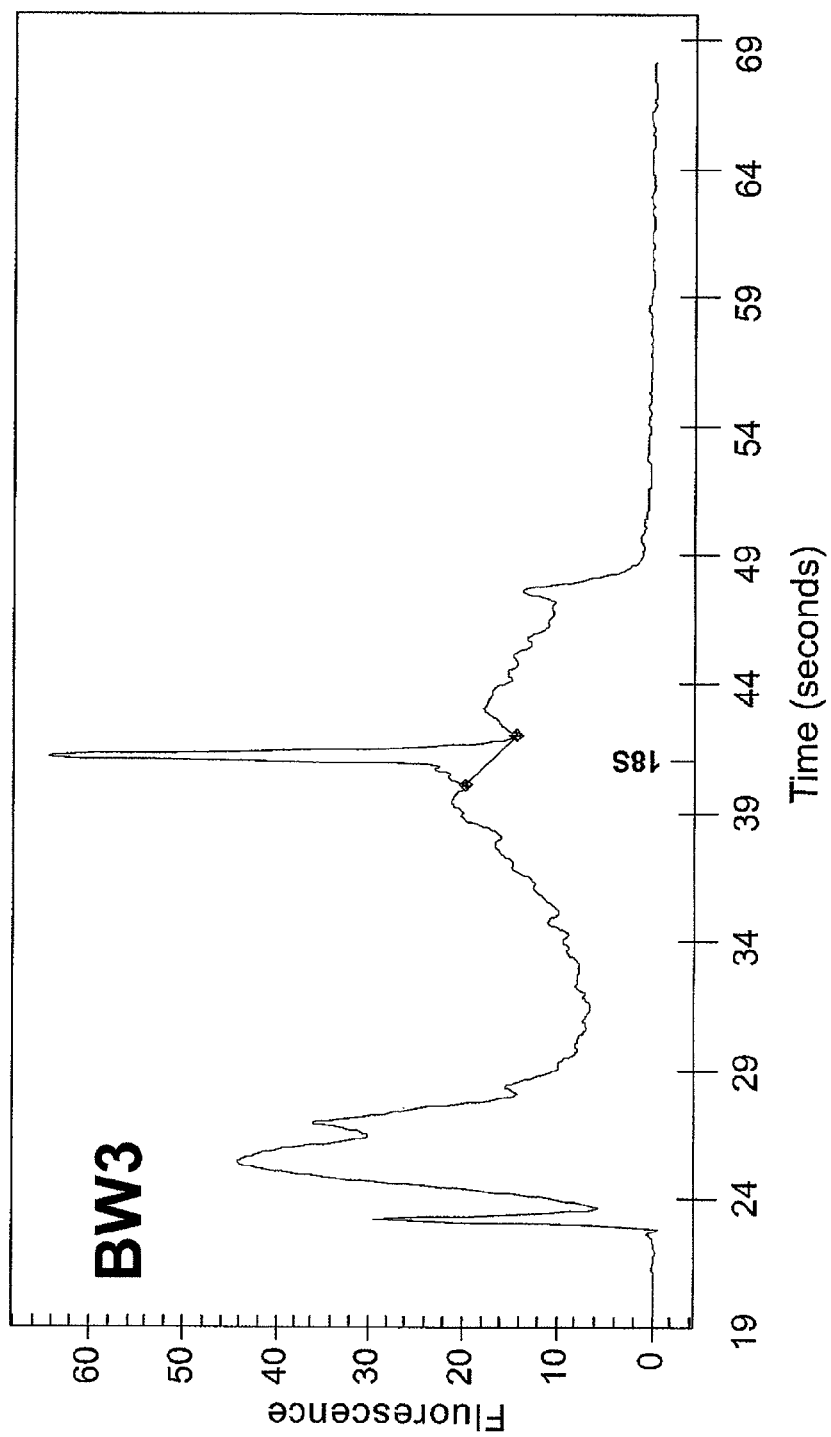
Figure 1E:
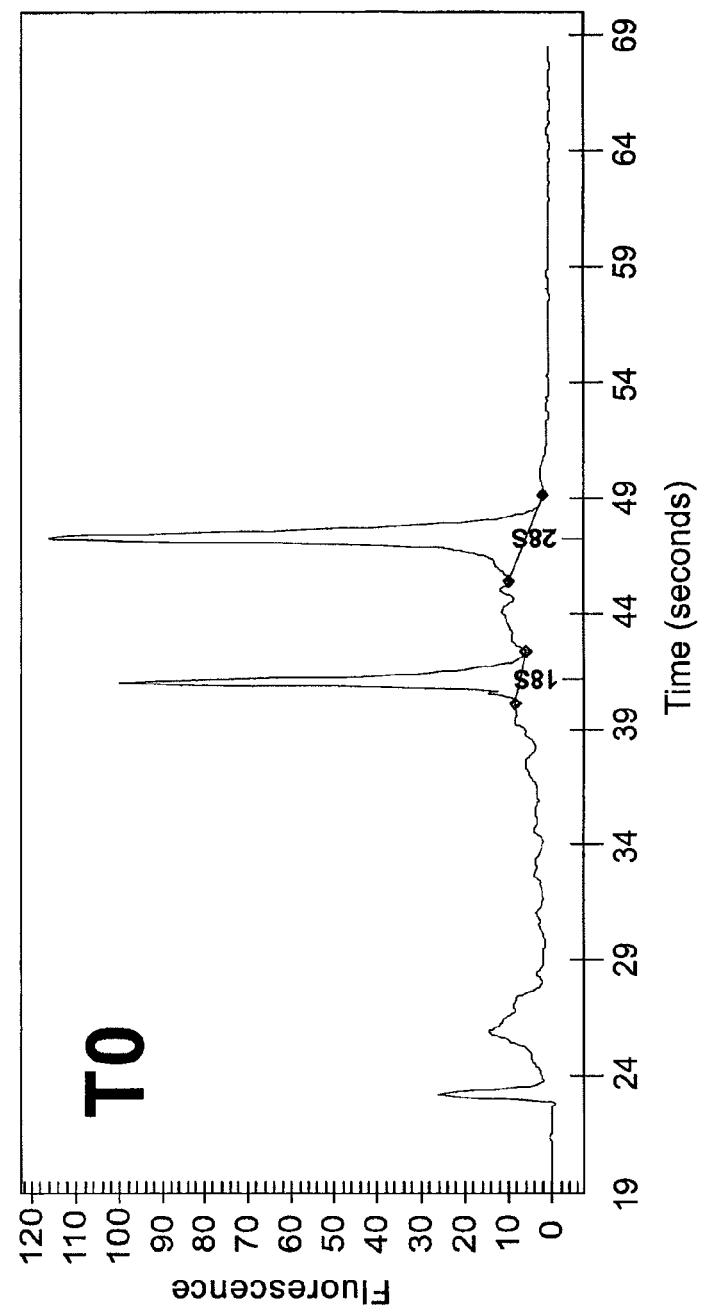
Figure 1F:
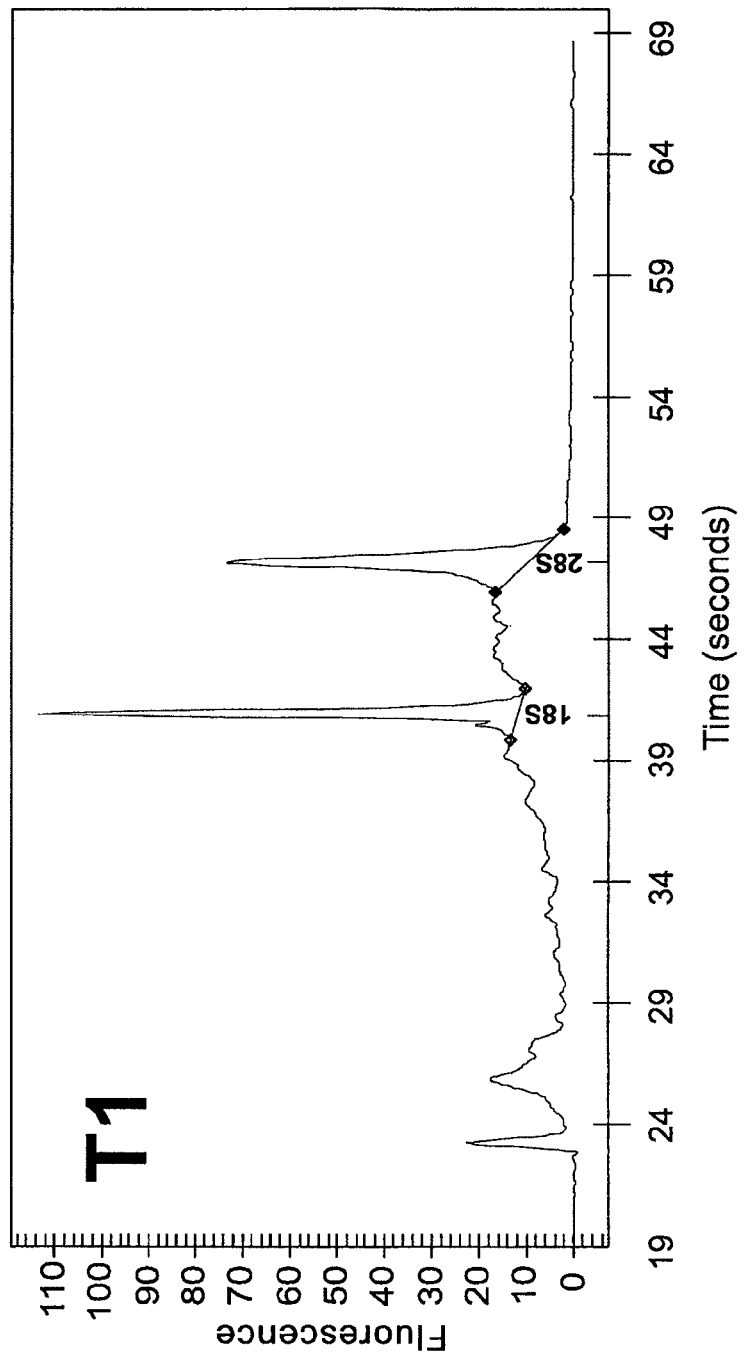
Figure 1G:
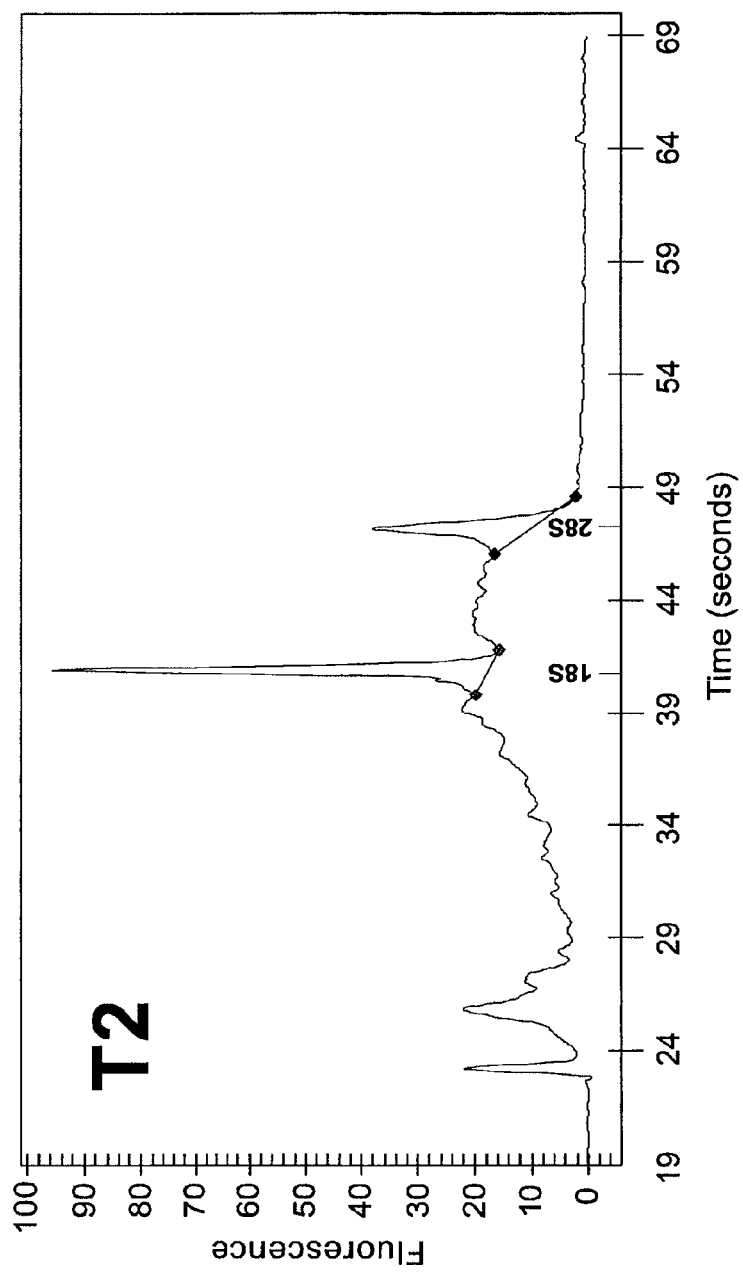
Figure 1H:
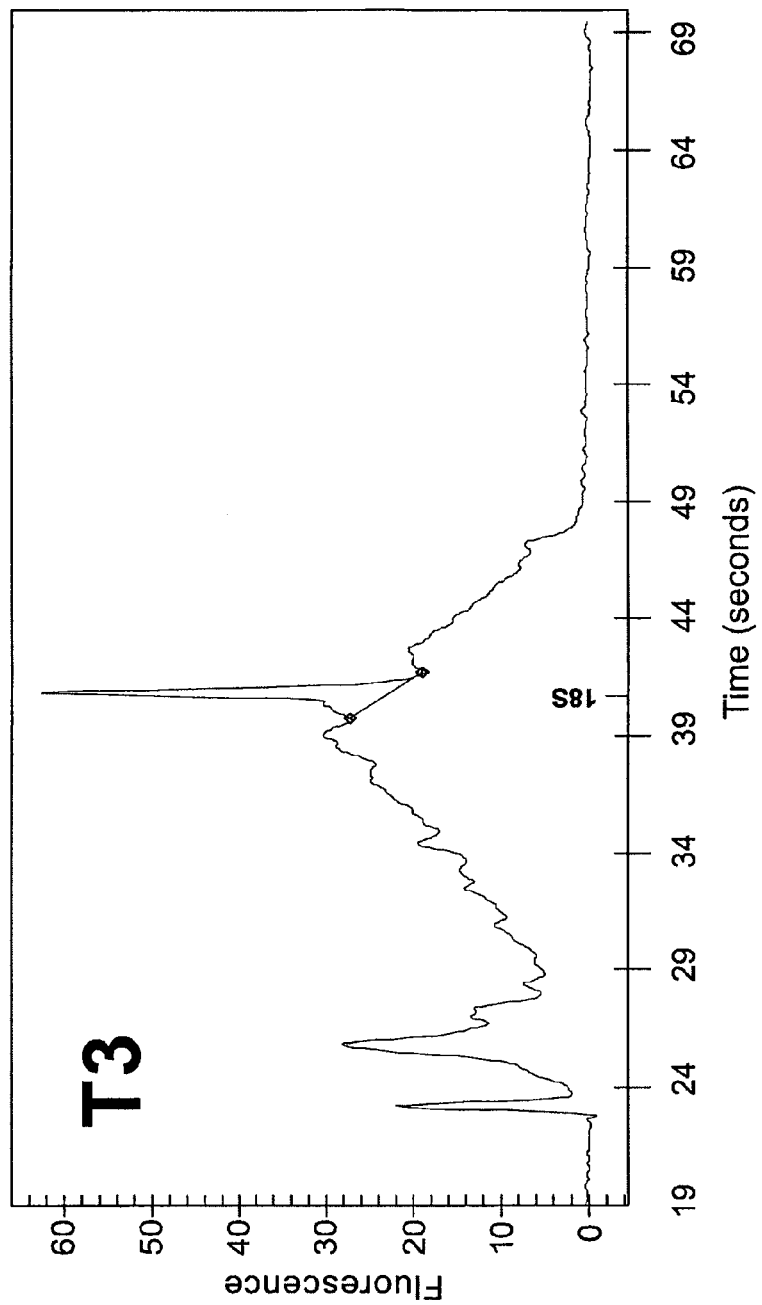
Figure 1I:
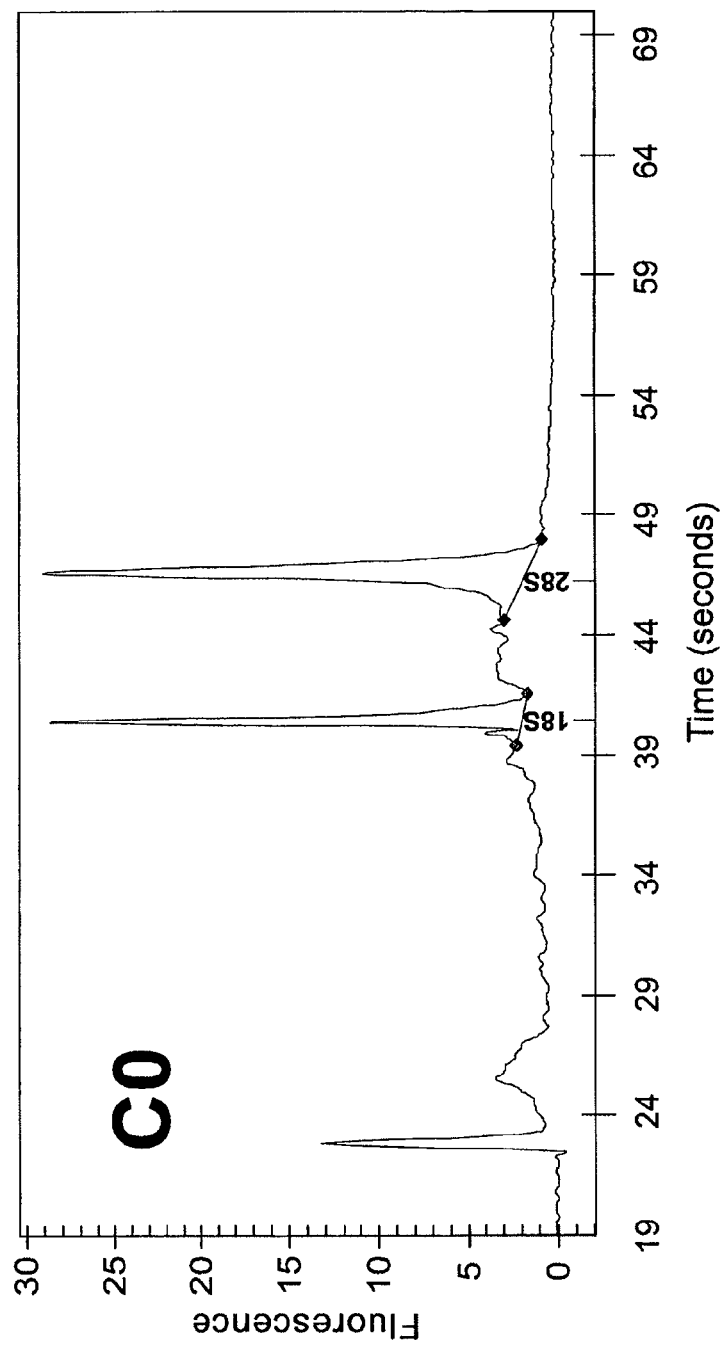
Figure 1J:
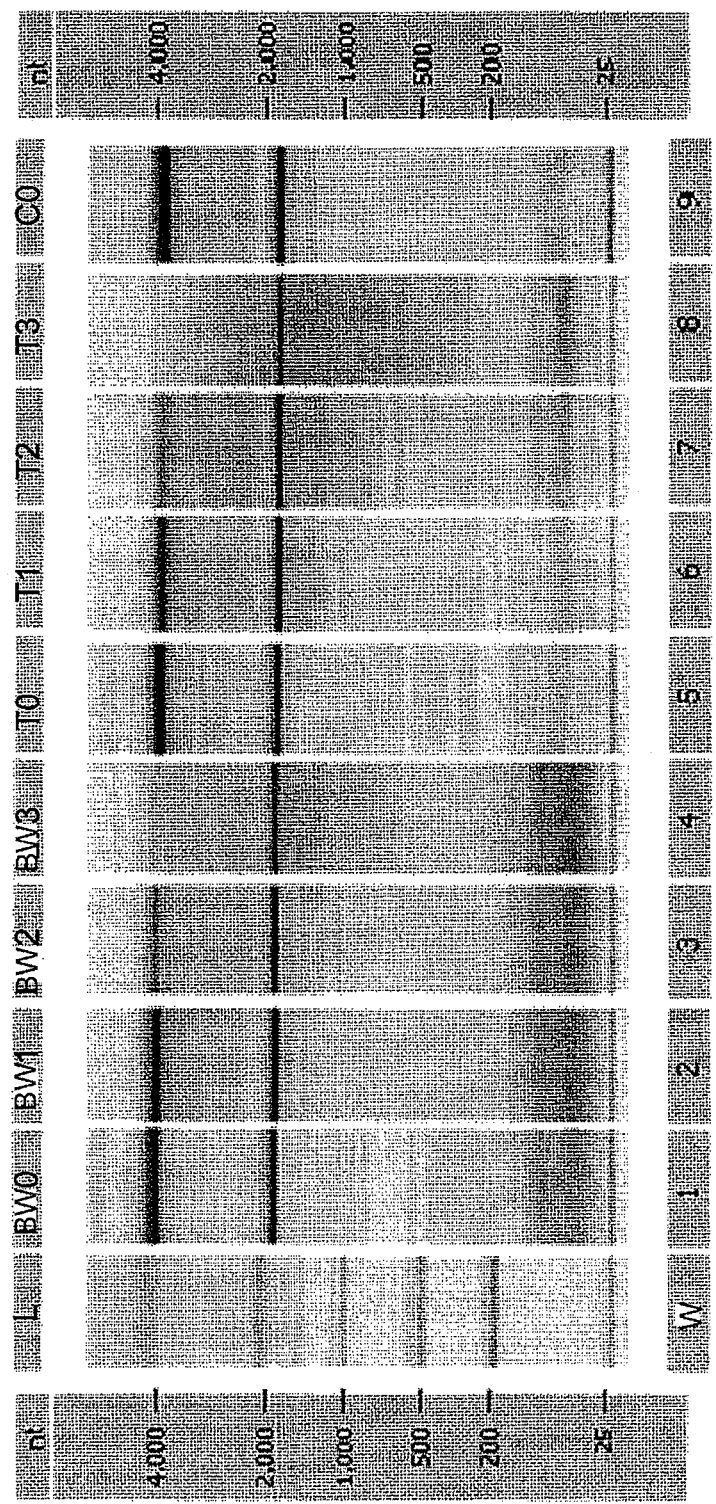

The object of the present invention relates to an in vitro non-invasive bladder cancer diagnosis and/or prognosis method based on the detection and quantification in bladder fluids of the gene expression of certain genes and/or combinations thereof acting as genetic markers of said disease.

Likewise, the use of said genes as bladder cancer diagnosis and/or prognosis genetic markers is an object of the present invention.

Finally, another object of the invention relates to a bladder cancer diagnosis and/or prognosis kit based on the use of said genes as genetic markers of the disease.

DESCRIPTION OF THE INVENTION

The main objective of the present invention is to develop an in vitro non-invasive bladder cancer diagnosis and/or prognosis method based on the detection and quantification of certain genes acting as genetic markers of the disease.

To carry out the method, the starting point is a bladder fluid sample obtained from a subject on which an analysis is conducted for the detection and quantification of the expression pattern of certain genes and/or combinations thereof. The results obtained are compared with the normal reference values for said genes in bladder fluids to thus establish the diagnosis and/or prognosis.

The term "subject" used in the present invention relates to a human being.

The bladder fluid sample obtained from the subject can be a urine or bladder washing sample and can be obtained by means of any conventional method.

In the present invention, bladder cancer diagnosis method is understood as that which allows detecting and quantifying differentially expressed genes between tumors and control samples (from healthy individuals) (diagnostic genes).

The prognosis method relates to those which allow detecting differentially expressed genes in the different types of tumors (prognostic genes), which allows classifying the tumors according to aggressiveness and personalizing the treatment in each case.

The tumor classification of the different types of transitional cell carcinomas (TCCs) is currently based on the macroscopic and microscopic observation in the pathological anatomy laboratory. Their classification is decided by means of more or less standardized observations, based on the depth of the tumor and on the microscopic appearance of the cells. Recent molecular studies seem to indicate that there are actually two differential genetic profiles which mostly separate superficial type tumors and infiltrating tumors.

Superficial bladder tumors are thus called Ta, Tis and T1. The Ta carcinoma is an exophytic carcinoma that is non-invasive or confined to the epithelium. Tis is a carcinoma in situ (flat superficial tumor) and T1 is a tumor invading the subepithelial connective tissue or invading the lamina propria.

In the present invention, the abbreviation HG is used to determine high-grade tumors and LG to determine low-grade tumors.

The Ta and T1 carcinomas can be extirpated by means of transurethral resection (TUR). Although high-grade (HG) Tis and T1 are superficial carcinomas confined to the mucosa, because they are high-grade tumors, it has been demonstrated with molecular biology techniques and by clinical experience that they have a high malignant and invasion potential.

In addition, infiltrating bladder carcinomas are classified into T2, T3 and T4. Thus, T2 relates to a tumor invading the muscular bladder layer. This type is in turn divided into T2a, invading the superficial muscular layer or the inner half, and T2b, invading the deep muscular layer or the outer half. T3 relates to a tumor invading beyond the muscular layer or invading the perivesical fat. This type is in turn divided into T3a, with microscopic invasion, and T3b, with macroscopic invasion. Finally, T4 relates to a tumor invading structures adjacent to the urinary bladder and which is in turn divided into T4a, with prostate, uterus or vagina invasion, and T4b, with pelvic wall or abdominal wall invasion.

The detection and quantification of the gene expression of the genes can be carried out by means of any non-invasive molecular biology technique suitable for the purposes of the invention, such as for example expression microarrays, quantitative real-time PCR, northern blot, conventional PCR, etc.

Specifically, the use of DNA arrays allows obtaining expression results of a very high number of genes, allowing to test thousands of genes in each experiment. The use of this technique requires large amounts of RNA with a good quality (non-degraded).

The quantitative real-time PCR technique (qRT-PCR) is preferably used in the present invention to detect and quantify the diagnostic and/or prognostic genes. This technique is more accurate, in addition to allowing the use of RNA with a considerable degree of degradation, without this affecting the end result. Likewise, it allows quantifying the specific RNA of the genes of interest. In particular embodiments, the hybridization probes used are Taqman probes.

The results obtained in the detection and quantification of the expression of the genes in the bladder fluid sample are compared with the normal reference values for said genes in samples from healthy subjects. The increase or the decrease of the marker genes levels are generally estimated by means of comparing the results obtained from the analysis of the samples corresponding to the subjects of the assay with the results of the control samples, which are analyzed in parallel. The final decision of the classification of each sample is made by means of an "alarm system" based on the expression values of the marker genes, such that if any of the values observed shows a very significant deviation in relation to what is expected in a control sample, the probability that a final classification is a tumor classification greatly increases, regardless of the gene which has "given the alarm".

More specifically, in a main aspect of the invention, the non-invasive bladder cancer diagnosis and/or prognosis method comprises collecting a bladder fluid sample from a subject to carry out the detection and quantification in said sample of the expression pattern of the combination of ANXA10, C14orf78, CTSE, CRH, IGF2, KLF9, KRT20, MAGEA3, POSTN, PPP1R14D, SLC1A6, TERT, ASAM and MCM10 genes. The results obtained were compared to the normal reference values for said genes in bladder fluids.

The bladder fluid sample is preferably urine, given that it is obtained much more easily. Nevertheless, bladder washing is occasionally done in a routine manner and RNA with a better quality is obtained The ANXA 10 (annexin A10) gene (also called ANX14), located in 4q32.3, participates in cell division regulation and in different signal transduction pathways, but their exact function has still not been determined.

The C14orf78 (chromosome 14 open reading frame 78) gene (also called AHNAK2 or KIAA2019) is located in 14q32.33. Its function has still not been determined.

The CTSE (cathepsin E) gene (also called CATE), located in 1q31, encodes an intracellular protease.

The CRH (corticotropin releasing hormone) gene (also called CRF), located in 8q13, encodes the corticotropin releasing hormone, secreted in the hypothalamus in response to stress.

The IGF2 (insulin-like growth factor 2 (somatomedin A)) gene (also called 11orf43, FLJ22066, FLJ44734, INSIGF), located in 11p15.5, encodes the insulin-like growth factor.

The KLF9 (Kruppel-like factor 9) gene (also called BTEB1) encodes a transcription factor.

The KRT20 (Keratin 20) gene (also called K20; CK20, KRT21; MGC35423), located in 17q21.2, encodes a protein forming part of the intermediate filaments in charge of giving structure and integrity to epithelial cells.

The MAGEA3 (melanoma antigen family A, 3) gene (also called HIP8; HYPD; MAGE3; MAGEA6; MGC14613) is located in Xq28. Its function is unknown.

The POSTN (periostin, osteoblast specific factor) gene (also called PN; OSF-2; PDLPOSTN; MGC119510, MGC119511, periostin; RP11-412K4.1) is located in 13q13.3 and has a function related to cell mobility.

The PPP1R14D (protein phosphatase 1, regulatory (inhibitor) subunit 14D) gene (also called GBPI-1; FLJ20251; MGC119014, MGC119016, CPI17-like) is located in 15q15.1 and encodes a phosphatase.

The SLC1A6 (solute carrier family 1 (high affinity aspartate/glutamate transporter), member 6) gene (also called EAAT4; MGC33092, MGC43671), located in 19p13.12, participates in intracellular transport.

The TERT (telomerase reverse transcriptase) gene (also called TP2; TRT; EST2; TCS1, hEST2), located in 5p15.33, encodes a polymerase of telomeres with reverse transcriptase activity.

The ASAM (adipocyte-specific adhesion molecule) gene (also called ASAM; ACAM; FLJ22415), located in 11q24.1, participates in cell adhesion.

Finally, the MCM10 (minichromosome maintenance deficient 10 (S. cerevisiae)) gene (also called CNA43; PRO2249, MGC126776), located in 10p13, encodes a protein involved in the initiation of genomic replication.

In another aspect of the invention, the in vitro non-invasive bladder cancer diagnosis and/or prognosis method comprises collecting a bladder fluid sample from a subject to carry out the detection and quantification in said sample of the expression pattern of the combination of ANXA10, CTSE, CRH, IGF2, KRT20, MAGEA3, SLC1A6, TERT, and MCM10 genes. The results obtained are compared with the normal reference values for said genes in bladder fluids.

In another aspect of the invention, the in vitro non-invasive bladder cancer diagnosis and/or prognosis method comprises collecting a bladder fluid sample from a subject to carry out the detection and quantification in said bladder fluid sample of the expression of a gene selected from C14orf78, KLF9, POSTN, PPP1R14D, ASAM and combinations thereof. The results obtained are compared with the normal reference values for said genes in bladder fluids.

Thus, in one particular aspect of the invention, said diagnosis and/or prognosis method based on the individual detection and quantification of the expression of the C14orf78 gene is contemplated.

In another particular aspect of the invention, said diagnosis and/or prognosis method based on the individual detection and quantification of the expression of the KLF9 gene is contemplated.

In another particular aspect of the invention, said diagnosis and/or prognosis method based on the individual detection and quantification of the expression of the POSTN gene is contemplated.

In another particular aspect, said diagnosis and/or prognosis method based on the individual detection and quantification of the expression of the PPPIR14D gene is contemplated.

In another particular aspect of the invention, said diagnosis and/or prognosis method based on the individual detection and quantification of the expression of the ASAM gene is contemplated.

In another particular embodiment of the invention, an in vitro non-invasive bladder cancer diagnosis and/or prognosis method based on the detection and quantification of a gene selected from C14orf78, KLF9, POSTN, PPP1R14D, ASAM and combinations thereof and, additionally, at least one gene selected from ANXA10, CTSE, CRH, IGF2, KRT20, MAGEA3, SLC1A6, TERT and MCM10 is contemplated.

In another aspect of the invention, an in vitro non-invasive method focused on bladder cancer diagnosis is contemplated which comprises collecting a bladder fluid sample from a subject to carry out the detection and quantification of the expression pattern of the combination of ANXA10, C14orf78, CTSE, CRH, IGF2, KLF9, KRT20, MAGEA3, POSTN, PPP1R14D, SLC1A6 and TERT genes, according to the previously described method. The results obtained are compared with the normal reference values for said genes in bladder fluids.

In another aspect of the invention, the in vitro non-invasive bladder cancer diagnosis method comprises collecting a bladder fluid sample from a subject to carry out the detection and quantification of the expression pattern of the combination of ANXA10, CTSE, CRH, IGF2, KRT20, MAGEA3, SLC1A6 and TERT genes. The results obtained are compared with the normal reference values for said genes in bladder fluids.

In another aspect of the invention, the in vitro non-invasive bladder cancer diagnosis method comprises collecting a bladder fluid sample from a subject to carry out the detection and quantification of the expression of a gene selected from C14orf78, KLF9, POSTN, PPP1R14D and combinations thereof. The results obtained are compared with the normal reference values for said genes in bladder fluids.

In a particular embodiment of the invention, said diagnosis method is based on the detection and quantification of the C14orf78 gene.

In another particular embodiment of the invention, said diagnosis method is based on the detection and quantification of the KLF9 gene.

In another particular embodiment of the invention, said diagnosis method is based on the detection and quantification of the POSTN gene.

In another particular embodiment of the invention, said diagnosis method is based on the detection and quantification of the PPPIR14D gene.

In another particular embodiment of the invention, said diagnosis method is based on the detection and quantification of the expression of a gene selected from C14orf78, KLF9, POSTN, PPP1R14D and combinations thereof and, additionally, at least one gene selected from ANXA10, CTSE, CRH, IGF2, KRT20, MAGEA3, SLC1A6 and TERT.

In another aspect of the invention, an in vitro non-invasive bladder cancer prognosis method is contemplated which comprises collecting a bladder fluid sample from a subject to carry out the detection and quantification of the expression pattern of the combination of ASAM and MCM10 genes. The results obtained are compared with the normal reference values for said genes in bladder fluids.

Another aspect of the invention provides an in vitro non-invasive bladder cancer prognosis method which comprises collecting a bladder fluid sample from a subject to carry out the detection and quantification of the expression of the ASAM gene. The results obtained are compared with the normal reference values for said gene in bladder fluids.

In another aspect of the invention, the use of the combination of ANXA10, C14orf78, CTSE, CRH, IGF2, KLF9, KRT20, MAGEA3, POSTN, PPP1R14D, SLC1A6, TERT, ASAM and MCM10 genes as bladder cancer diagnosis and/or prognosis markers is contemplated.

Another aspect of the invention is focused on the use of the combination of ANXA10, CTSE, CRH, IGF2, KRT20, MAGEA3, SLC1A6, TERT, and MCM10 genes as bladder cancer diagnosis and/or prognosis markers.

In another aspect of the invention, the use of a gene selected from C14orf78, KLF9, POSTN, PPP1R14D, ASAM and combinations thereof as bladder cancer diagnosis and/or prognosis markers is contemplated.

In a particular embodiment of the invention, the use of the C14orf78 gene as a bladder cancer diagnosis and/or prognosis marker is contemplated.

In another particular embodiment of the invention, the use of the KLF9 gene as a bladder cancer diagnosis and/or prognosis marker is contemplated.

In another particular embodiment of the invention, the use of the POSTN gene as a bladder cancer diagnosis and/or prognosis marker is contemplated.

In another particular embodiment of the invention, the use of the PPP1R14D gene as a bladder cancer diagnosis and/or prognosis markers is contemplated.

In another particular embodiment of the invention, the use of the ASAM gene as a bladder cancer diagnosis and/or prognosis marker is contemplated.

Another aspect of the invention is focused on the use of a gene selected from C14orf78, KLF9, POSTN, PPP1R14D, ASAM and combinations thereof, in combination with at least one gene selected from ANXA10, CTSE, CRH, IGF2, KRT20, MAGEA3, SLC1A6, TERT and MCM10, as bladder cancer diagnosis and/or prognosis markers.

Another aspect of the invention relates to the use of the combination of ANXA10, C14orf78, CTSE, CRH, IGF2, KLF9, KRT20, MAGEA3, POSTN, PPP1R14D, SLC1A6 and TERT genes as bladder cancer diagnosis markers.

Another aspect of the invention is focused on the use of the combination of ANXA10, CTSE, CRH, IGF2, KRT20, MAGEA3, SLC1A6 and TERT genes as bladder cancer diagnosis markers.

Another aspect of the invention relates to the use of a gene selected from C14orf78, KLF9, POSTN, PPP1R14D and combinations thereof as bladder cancer diagnosis markers.

In a particular embodiment of the invention, the use of the C14orf78 gene as a bladder cancer diagnosis marker is contemplated.

Likewise, in another particular embodiment of the invention, the use of the KLF9 gene as a bladder cancer diagnosis marker is contemplated.

In another particular embodiment of the invention, the use of the POSTN gene as a bladder cancer diagnosis marker is contemplated.

In another particular embodiment of the invention, the use of the PPP1R14D gene as bladder cancer diagnosis markers is contemplated.

In another aspect of the invention, the use of a gene selected from C14orf78, KLF9, POSTN, PPP1R14D and combinations thereof, in combination with at least one gene selected from ANXA10, CTSE, CRH, IGF2, KRT20, MAGEA3, SLC1A6 and TERT, as bladder cancer diagnosis markers is contemplated.

In another aspect of the invention, the use of the combination of ASAM and MCM10 genes as bladder cancer prognosis markers is contemplated.

In another aspect of the invention, the use of the ASAM gene as a bladder cancer prognosis marker is contemplated.

Another aspect of the invention relates to a bladder cancer diagnosis and/or prognosis kit comprising a set of probes suitable for the detection and quantification of the expression pattern of the combination of ANXA10, C14orf78, CTSE, CRH, IGF2, KLF9, KRT20, MAGEA3, POSTN, PPP1R14D, SLC1A6, TERT, ASAM and MCM10 genes.

In another aspect of the invention, the bladder cancer diagnosis and/or prognosis kit comprises a set of probes suitable for the detection and quantification of the expression pattern of the combination of ANXA10, CTSE, CRH, IGF2, KRT20, MAGEA3, SLC1A6, TERT and MCM10 genes.

In another aspect of the invention, a bladder cancer diagnosis and/or prognosis kit based on a set of probes suitable for the detection and quantification of a gene selected from C14orf78, KLF9, POSTN, PPP1R14D, ASAM and combinations thereof is contemplated.

In a particular embodiment of the invention, said bladder cancer diagnosis and/or prognosis kit, based on the set of probes for the detection and quantification of a gene selected from C14orf78, KLF9, POSTN, PPP1R14D, ASAM and combinations thereof, additionally comprises a set of probes suitable for the detection and quantification of a gene selected from ANXA10, CTSE, CRH, IGF2, KRT20, MAGEA3, SLC1A6, TERT and MCM10.

In another aspect of the invention, a bladder cancer diagnosis kit, based on a set of probes suitable for the detection and quantification of the expression pattern of the combination of ANXA10, C14orf78, CTSE, CRH, IGF2, KLF9, KRT20, MAGEA3, POSTN, PPP1R14D, SLC1A6 and TERT genes, is contemplated.

In another aspect of the invention, the bladder cancer diagnosis kit comprises a set of probes suitable for the detection and quantification of the expression pattern of the combination of ANXA10, CTSE, CRH, IGF2, KRT20, MAGEA3, SLC1A6 and TERT genes.

In another aspect of the invention, the cancer diagnosis kit based on a set of probes suitable for the detection and quantification of a gene selected from C14orf78, KLF9, POSTN, PPP1R14D and combinations thereof is contemplated.

In another aspect of the invention, said kit, based on the set of probes suitable for the detection and quantification of a gene selected from C14orf78, KLF9, POSTN, PPP1R14D and combinations thereof, additionally comprises probes suitable for the detection and quantification of at least one gene selected from ANXA10, CTSE, CRH, IGF2, KRT20, MAGEA3, SLC1A6 and TERT.

In another aspect of the invention, a bladder cancer prognosis kit, based on a set of probes suitable for the detection and quantification of the expression pattern of the combination of ASAM and MCM10 genes, is contemplated.

In another aspect of the invention, the prognosis kit is based on a probe suitable for the detection and quantification of the ASAM gene.

Table 1 shows the 14 genes identified as bladder cancer diagnosis and/or prognosis genetic markers. The ASAM and MCM10 genes are the 2 specific genes for prognosis.

Several examples which are useful for illustrating but not for limiting the present invention are set forth below.

EXAMPLES

Example 1

Determination of the Importance of Degradation in Bladder Fluid Samples

To carry out the final objective of the invention, it was first necessary to know the impact of different RNA degradation levels on gene expression profiles, given that the quality of the RNA obtained from bladder fluids (urine and/or bladder washing) is generally low. It also had to be determined if the gene expression profiles obtained from the bladder fluids matched those obtained in the corresponding tumors.

1. Selection of Samples and RNA Preparation

A tumor tissue (T) and bladder washing (BW) sample from one and the same patient diagnosed as high-grade (G3) pT2 was selected [according to the methods described in Lopez-Beltran A, Sauter G, Gasser T, Hartmann A, Schmitz-Drager B J, Helpap B, Ayala A G, Tamboni P, Knowles M A, Sidransky D, Cordon-Cardo C, Jones P A, Cairns P, Simon R, Amin M B, Tyczynsky J E. Tumours of the Urinary System. In: Eble J N, Sauter G, Epstein J I, Sesterhenn I A (eds.), *Pathology and Genetics of Tumours of the Urinary System and Male Genital Organs. World Health Organization Classification of Tumours. Lyon: IARC Press;* 2004: 89-157; Sobin L H, Wittekind C H. *TNM Classification of Malignant Tumours. International Union Against Cancer.*, 6th ed. New York: John Wiley & Sons; 2002]. The RNA of both samples (T0 and BW0) was extracted with TRIzol (Invitrogen, Carlsbad, Calif., USA) according to the supplier's instructions. Aliquots of both RNAs (T0 and BW0) were then degraded by incubating them at 80° C. for 15 (T1 and BW1), 30 (T2 and BW2) and 60 (T3 and BW3) minutes, obtaining three degradation levels, as described in Xiang C C, Chen M, Ma L et al. *A new strategy to amplify degraded RNA from small tissue samples for microarray studies. Nucleic Acids Res* 2003; 31:53, with the exception that water was used instead of a basic buffer.

Healthy bladder mucosa samples from 4 patients without evidence of bladder pathology (control samples) were also collected, RNA was obtained in the same manner as with the previous samples and the 4 RNAs were mixed in equimolar ratios (C0).

One μl of each of the intact and degraded RNAs were analyzed in the Agilent 2100 Bioanalyzer to determine the quality of each RNA (according to the method described in Imbeaud S, Graudens E, Boulanger V et al. *Towards standardization of RNA quality assessment using user-independent classifiers of microcapillary electrophoresis traces. Nucleic Acids Res* 2005; 33:e56) (FIGS. 1.A-H). FIG. 1 (J) shows the gel with the bands of the ribosomal RNAs (28S and 18S) of each of the analyzed samples in which the progressive degradation of these bands is observed.

In addition, 36 tumor bladder washings (8 low-grade (LG) pTa, 5 high-grade (HG) pTa, 3 pT1 LG, 5 pT1 HG, 4 pTis, 9 pT2 HG and 2 pT4 HG) and 14 control bladder washings from patients without bladder pathology were collected and the RNA was extracted in the same manner as in the previous cases.

2. In vitro RNA Amplification and Labeling

5 µg of intact RNA (T0 and BW0) and degraded RNA (T1, T2, T3, BW1, BW2 and BW3) were amplified by means of using primers with a random sequence of 9 nucleotides (random nonamer primers) modified by the addition in 3' of the T3 promoter sequence (T3N9) (according to Xiang C C, Chen M, Ma L et al. *A new strategy to amplify degraded RNA from small tissue samples for microarray studies. Nucleic Acids Res* 2003; 31:e53). The probes were synthesized by means of a direct labeling method (according to Richter A, Schwager C, Hentze S, Ansorge W, Hentze M W, Muckenthaler M. *Comparison of fluorescent tag DNA labeling methods used for expression analysis by DNA microarrays. Biotechniques* 2002; 33:620-8, 630).

3. Array Processing and Data Analysis

Figure 2:
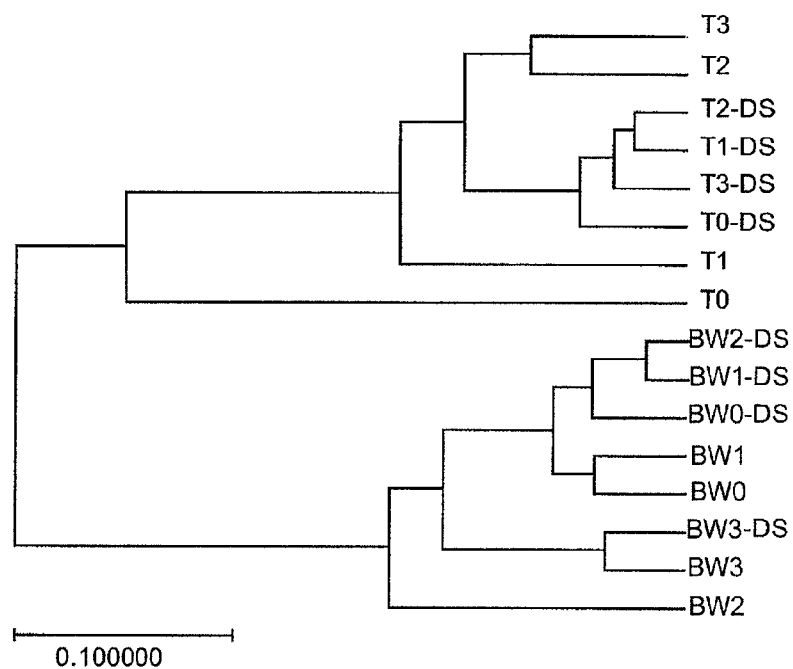
FIG. 2: (a) Semi-matrix of comparison between pairs of arrays of the 100 most differentially expressed genes in each array. The upper and lower part shaded in gray of the semi-matrix shows the percentage of differentially expressed genes in common between the pairs of bladder washing (BW) arrays and between the pairs of tumors (T) arrays, hybridized with RNA of a different degree of degradation. The non-shaded part of the semi-matrix corresponds to the percentage of differentially expressed genes in common between the pairs of bladder washing and tumor arrays. (b) Unsupervised cluster of all the clones contained in the microarray, including the duplicates with dye swap (DS).

Oncochip-v2 glass human cDNA microarrays were used to co-hybridize each of the four progressively degraded aliquots of RNA, both of tumor and of bladder washing (T0, T1, T2, T3, BW0, BW1, BW2 and BW3), with the pool of the RNAs from healthy bladder mucosa samples (C0). The fluorescent images were obtained with the G2565BA Microarray Scanner System (Agilent, Technologies, Waldbronn, Germany) and the TIFF images were quantified using the Spot program which is available from the Commonwealth Scientific and Industrial Research Organization (CSIRO) of Australia under the R statistical environment which is available from the database hosted by the Institute for Statistics and Mathematics of Wirtschaftsuniversität Wien. The final intensity measurement of each point of the microarray was calculated as had been previously suggested in the Microarray DATA Analysis Group managed by "Speed Berkeley Research Group", University of Berkeley, Berkeley, Caliif. (publicly accessible data in the GEO database; GSE3192). Finally, 1111 valid clones were obtained which complied with all the quality criteria and the 100 most differentially expressed clones of each array were chosen to compare between arrays and calculate the percentages of genes in common between them. A high percentage of differentially expressed genes in common was detected between the tumor tissue arrays (85 to 91%) and between the bladder washing arrays (78 to 93%) (FIG. 2*a*), which indicated that RNA degradation virtually did not affect the gene expression profiles.

An unsupervised cluster of all the clones contained in the microarray was also carried out using UPGMA (Unweighted Pair Group Method with Arithmetic mean) and Pearson's correlation. This cluster indicated that the percentage of genes in common identified between 2 arrays hybridized with RNA with a different degradation level (for example, BW0 and BW1) was occasionally higher than the percentage between dye swap (DS) duplicates of the same array (for example, BW0 vs. BW0-DS) (FIG. 2*b*), which reinforced the conclusion that the gene expression profiles were virtually not altered when working with partially degraded RNA.

To determine if the gene expression profiles obtained from the bladder washing samples matched those obtained in the corresponding tumor, the percentage of differentially expressed genes in common between the tumor tissue arrays and the bladder washing arrays was compared. A high similarity between the tumor and the bladder washing was obtained (52 to 60%) and this similarity was independent of the RNA degradation condition.

In conclusion, this data suggested that partially degraded bladder washing RNA could be used for gene expression studies using microarrays and that this RNA is a reflection of the gene expression of the tumor.

4. Quantitative Real-time RT-PCR (qRT-PCR)

To validate that the results obtained in the microarrays of a particular patient could be extrapolated to a longer cohort, 4 differentially expressed genes in the arrays which were related to the bladder carcinogenesis process according to the literature (KRT20, IGF2, GSN and CCL2) were analyzed by means of qRT-PCR. For this validation, 36 additional tumor bladder washings and 14 control bladder washings were used.

The cDNA was synthesized from 1 ug of RNA using the High-Capacity cDNA Archive Kit (Applied Biosystems, Foster City, USA) according to the supplier's instructions, except that the final volume of the reaction was reduced to 50 µl. The GUSB gene was used as an endogenous control. The PCRs were carried out using Assays-on-Demand™ Gene Expression Products in an ABI PRISM 7000 SDS (Applied Biosystems, Foster City, USA) according to the supplier's instructions, except that the volume of the reaction was reduced to 20 µl.

The ΔΔCt method (ABI PRISM 7700 Sequence Detection System User Bulletin #2: Relative Quantification of Gene Expression P/N 4303859) was used to calculate the relative amount of expression of each gene in relation to an average of the expression of the 14 control samples. To establish the reference value in the controls, the arithmetic mean of the expression values of the 14 control bladder washings from patients without bladder pathology was obtained.

Figure 3:
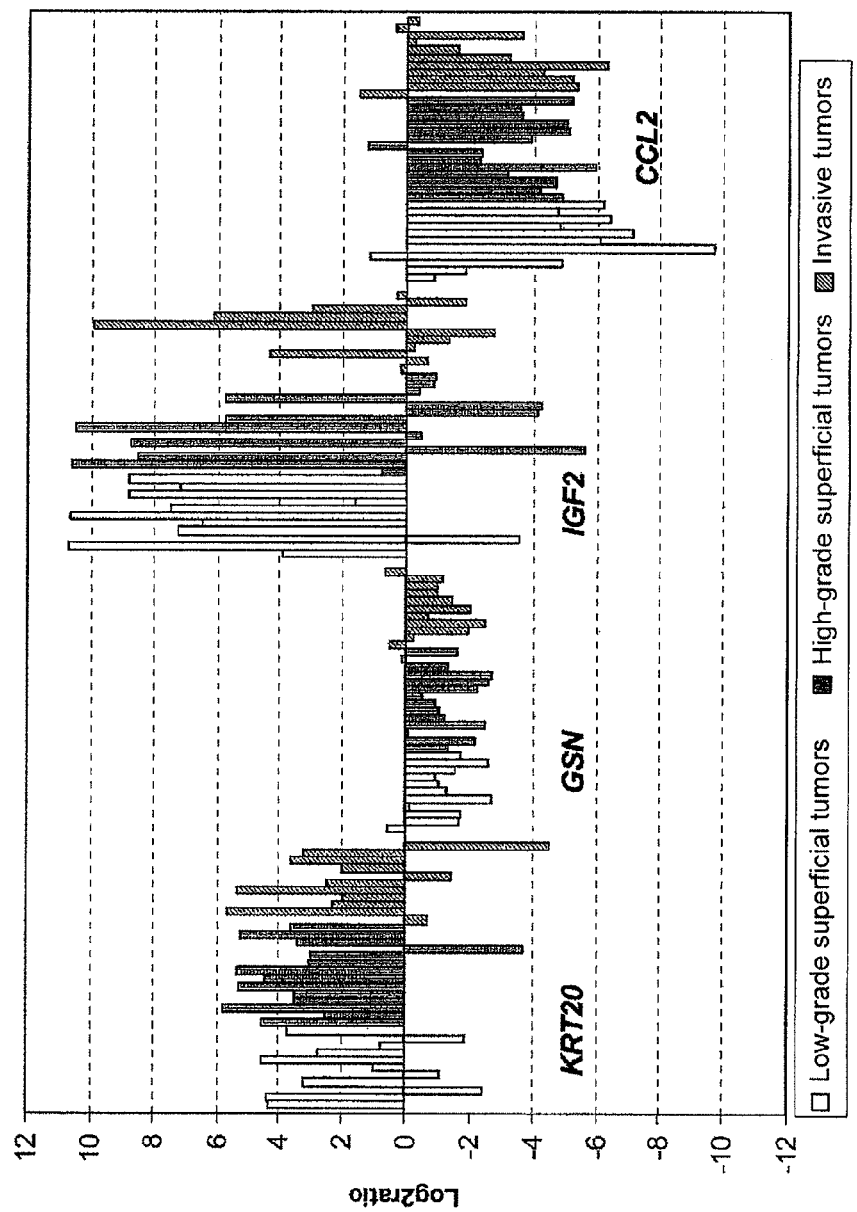
FIG. 3: Validation by means of quantitative real-time RT-PCR (qRT-PCR) of 4 differentially expressed genes (KRT20, GSN, IGF2 and CCL2) in the cDNA microarrays and related to bladder cancer, in 36 additional tumor bladder washing samples. The positive values indicate overexpression in the tumor bladder washings in relation to the controls. The samples are grouped in the graph depending on the log 2ratio according to the tumor stage and grade: low-grade superficial tumors (8 pTa and 3 pT1), high-grade superficial tumors (5 pTa, 5 pT1 and 4 pTis) and invasive tumors (9 pT2 and 2 pT4).

The results of this analysis, expressed as log 2ratio, defined as the proportion or division (ratio) between the 2 compared conditions (in this case the endogenous control against each gene indicated) expressed as a base 2 logarithm, confirmed the results of the microarrays in 81% of the samples for KRT20, in 89% for GNS, in 64% for IGF2 and in 89% for CCL2 (FIG. 3). The high consistency between the microarray data obtained from the analysis of a single patient and the qRT-PCR data obtained from the analysis of a cohort of 36 additional patients confirmed that the gene expression profiles obtained in the microarrays were not due to the analysis of a single patient.

5. Conclusion of Example 1

It is possible to use bladder washing RNA to deduce the gene expression profiles of the corresponding bladder tumors, both by means of cDNA microarrays and of qRT-PCR.

Example 2

Initial Determination of Candidate Genes for the Predictive Model

Once it was known that it was possible to determine gene expression profiles in bladder fluid samples, the next objective was to obtain characteristic gene expression data that was as extensive as possible. The decision was made to follow the strategy of starting by analyzing the largest possible amount of genes in a reduced number of samples, in order to progressively analyze an increasingly smaller and more selected amount of genes in a more extensive series of samples in successive phases.

The protocol in turn involved the establishment of very strict quality controls in all the critical steps of the process. This included obtaining biological samples with the desired characteristics in the operating room by surgeons of the Fundació Puigvert team, storing and preserving the samples in the suitable conditions, the anatomical-pathological analysis of the samples and the molecular processing by the laboratory equipment.

1. Obtaining and Selecting the Biological Samples

The tissue samples were obtained in the operating room using a cold forceps resector (tumor samples) or directly with scissors (control samples). Part of the tissue obtained was immediately frozen at −80° C. until being subsequently processed for RNA extraction and remaining part was sent to the Pathological Anatomy department for its anatomical-pathological analysis. For the RNA extraction, the tissues were mechanically homogenized and the RNAs were extracted according to the protocol of TRIzol (Invitrogen, Carlsbad, Calif., USA). Finally, the RNAs were quantified by spectrophotometrically measuring the absorbance at 260 nm.

2. Groups of Samples to be Studied

Given that superficial tumors and invasive tumors seem to have different genetic profiles, the decision was made to compare the most extreme tumor groups (low-grade superficial tumors versus infiltrating tumors). Furthermore, the decision was also made to find out the molecular profile of a type of tumor with an unclear clinical behavior, because they are tumors that are superficial but have a high degree of cell aberrations (classified as high-grade T1, pT1 HG) and in many case (about 50%) end up being infiltrating tumors. Four study groups were thus defined:

Group 1; low-grade (LG) superficial tumor samples which only invade the bladder mucosa (pathologically classified as pTa LG).

Group 2: high-grade (HG) superficial tumor samples which invade the subepithelial connective tissue (pathologically classified as pT1 HG).

Group 3: infiltrating and high-grade tumor samples (pathologically classified as pT2).

Group 4: healthy bladder mucosa samples (control).

For the purpose of reducing the biological variance, which was rather high, pools of samples of one and the same tumor type, i.e., with a same anatomical-pathological classification were carried out. Thus, 3 pools of 4-5 tumor samples were carried out for each of the groups; pTa LG, pT1 HG, pT2 HG and controls.

3. Affymetrix Microarrays

Although a platform of microarrays based on cDNA had been previously worked with, it was known from the literature that there were other commercial platforms based on oligonucleotides which would allow obtaining expression results of a higher number of genes. Finally, the decision was made to use the Affymetrix platform given that there was a large amount of data available in the public database for this platform, virtually all the references mentioned its high results quality and a new microarray (U133 plus 2.0) had just been launched on the market which allowed determining the gene expression of most human genes.

The Affymetrix microarrays were hybridized and scanned by a specialized company (Progenika) and the raw expression data (or cel files) were directly analyzed under the R statistical environment using the RMA (Robust Multi array Analysis) algorithm.

4. Affymetrix Microarray Analysis

Figure 4:
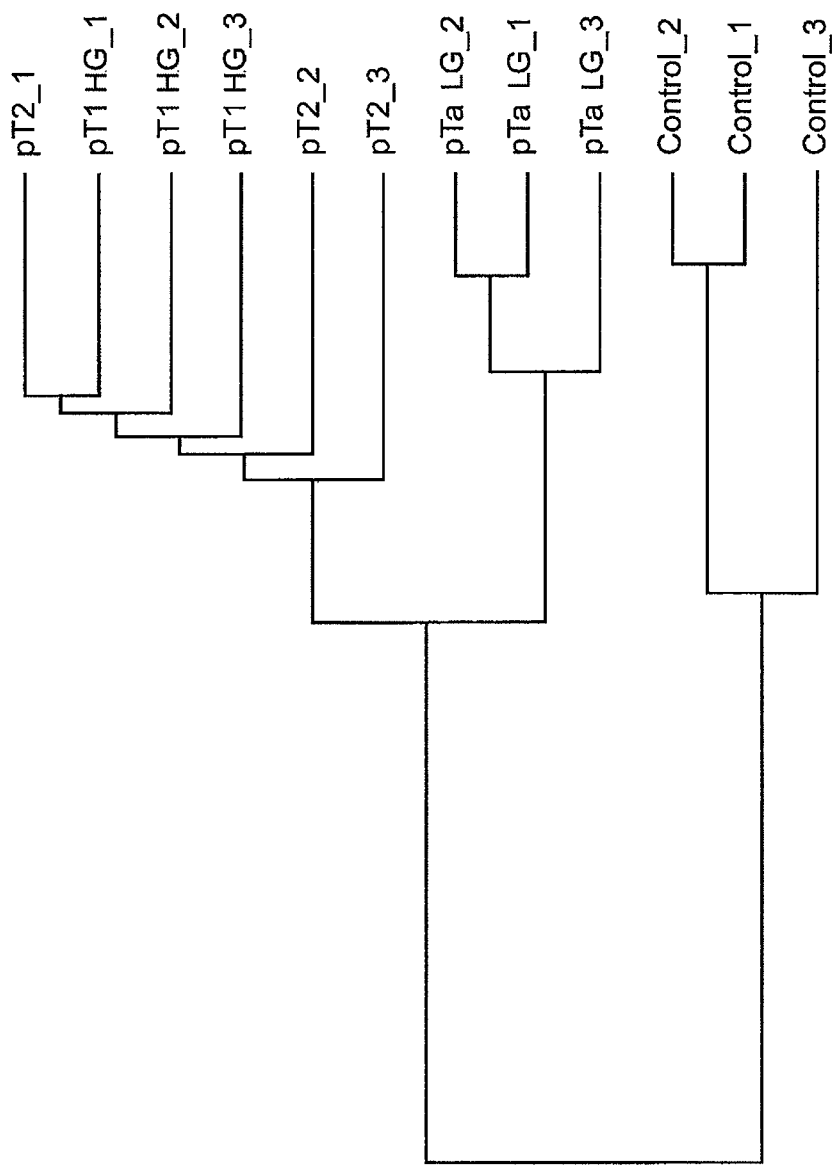
FIG. 4: Classification of the samples by means of unsupervised global cluster (Euclidean distance and UPGMA). pT2_1, pT2_2 and pT2_3 (infiltrating tumors); pT1 HG_1, pT1 HG_2 and pT1 HG_3 (high-grade superficial tumors); pT1 LG_1, pT1 LG_2, pT1 LG_3 (low-grade superficial tumors).

Once the standardized expression data for each clone had been obtained, the decision was made to study how the different samples which had been selected clustered together by carrying out an unsupervised cluster (FIG. 4). In the latter, it could be observed that all the controls were clustered together and clearly differentiated from the tumors, which indicated that there are many differentially expressed genes between tumors and controls (diagnostic genes). In addition, it is also observed that the 3 pools of infiltrating tumors (pT2_1, pT2_2 and pT2_3) and high-grade superficial tumors (pT1 HG_1, pT1 HG_2 and pT1 HG_3) are clustered together and differentiated from the 3 pools of low-grade superficial tumors (pT1 LG_1, pT1 LG_2, pT1 LG_3), which should allow locating marker genes of either pathway (prognostic genes).

As a ranking system for comparing the different groups and obtaining the best differentially expressed genes, the decision was made to use the ratio between the maximum intensity value of the group with the lowest mean and the minimum intensity value of the group with the highest mean, in a logarithmic scale. This measurement is equivalent to the minimum fold change which could be obtained by comparing any replica of a group against any replica of the other group. The end result obtained were literally thousands of genes with sufficiently significant expression differences between tumors and controls.

5. Validation of the Microarrays Results by Means of Quantitative Real-Time PCR

Once the genes were ordered from more to less differentially expressed, the decision was made to verify the results obtained with a completely independent and, according to the literature, much more accurate technique, quantitative real-time PCR (qRT-PCR). Ten of the most differentially expressed genes were selected to carry out this technical verification and their gene expression was quantified by means of qRT-PCR using exactly the same pools hybridized in the microarrays (in order to be able to compare the results of both techniques) and using the individual samples of each pool (in order to be able to study the replicability of the actual qRT-PCR technique) (FIG. 5). A regression coefficient of 0.978 was obtained in the comparison between microarrays and qRT-PCR, which indicated a very good replicability between the 2 techniques. When the arithmetic means of the individual samples obtained by means of qRT-PCR and their expression in the pools by means of the same technique were compared, the regression coefficient was 0.995, which confirmed that the bibliographic data of the fact that the quantification by means of qRT-PCR has an excellent technical quality.

6. Conclusion of Example 2

Taking into account the results observed by means of the quantification of gene expression using two completely independent techniques in a small group of genes, it can be extrapolated that the expressions observed by means of microarrays seem to be sufficiently reliable for being used to define a robust group of candidate genes for a subsequent, more extensive and specific analysis.

In parallel, it was concluded that although the microarrays were suitable for quantifying gene expressions, qRT-PCR was still more accurate, in addition to allowing higher RNA degradation levels in the sample without this negatively affecting the end result.

Example 3

First Selection of Candidate Genes

The final objective of this study was to select a reduced group of genes related to bladder TCC and that diagnostic and prognostic tumor information were obtained upon quantifying their expression. To that end, it has been verified that two techniques can be used, DNA microarrays and quantitative real-time PCR. By means of the microarray technology, thousands of genes are tested in each experiment and a larger amount of RNA with a better quality is needed to conduct the experiments than with the qRT-PCR methodology. Furthermore, the latter is a more accurate technology and the exact number of genes of interest can be quantified. Therefore, the decision was made to use the TaqMan Low Density Array (TLDA) technology, based on qRT-PCR, in the subsequent phases of the study.

1. Selection of 384 Genes for the TaqMan Low Density Arrays (TLDA) Cards

TLDA are microfluidic cards containing the lyophilized primers and TaqMan probe for a maximum of 384 genes (there are different TLDA configurations which allow analyzing from 384 genes in one and the same card and up to 48 genes and 8 samples in one and the same sample). Therefore, from the previously conducted experiments by means of Affymetrix microarrays hybridized with tissue RNA, a subgroup of 384 genes has to be selected. The most differentially expressed genes between tumors and controls (diagnostic genes) and also the differentially expressed genes between the three tumor groups: pTa LG, pT1 HG and pT2 HG (prognostic genes) were selected.

In addition, given that one of the objectives of the project was to work with bladder fluids, the intention in this phase of the project was to be able to study these 384 genes not with tissue RNA, as had been done up until now, but rather directly with bladder fluids (urine or bladder washings).

2. Collection and Processing of the Bladder Washings and Urine

The bladder washing samples were collected by barbotage intraoperatively, before the resection of the bladder tumor or before cystectomy. The urine samples were collected by spontaneous urination before the patient entered into surgery. Both the bladder washing samples and the urine sample were transported to the laboratory in ice immediately after being collected. The samples were mixed with ⅕ volumes of 0.5M EDTA, pH 8.0 and were centrifuged at 1000×g for 10 minutes. The cell pellets were resuspended in 1 ml of TRIzol (Invitrogen, Calsbad, Calif., USA) and were frozen at −80° C. until the RNA extraction.

425 tumor bladder washing samples, 30 control bladder washing samples, 43 tumor urine samples and 158 control urine samples were collected and stored.

3. RNA Extraction and cDNA Synthesis

The RNAs were extracted according to the protocol of TRIzol (Invitrogen, Calsbad, Calif., USA) and were quantified by spectrophotometrically measuring the absorbance at 260 nm.

The cDNA was synthesized from 1 ug of RNA using the High-Capacity cDNA Archive Kit (Applied Biosystems, Foster City, USA) according to the supplier's instructions, except that the final volume of the reaction was reduced to 50 µl.

4. Selection of "Taqman Gene Expression Products" and Quantitative Real-time RT-PCR (qRT-PCR).

Once the genes of interest were known, the primers and fluorescent probe (TaqMan Assays-on-Demand™ Gene Expression Products) were selected for the quantification of the gene expression by means of qRT-PCR in the Applied Biosystems web.

A microfluidic card (TaqMan Low Density Array, TLDA) was configured which contained 384 assays corresponding to diagnostic genes and prognostic genes and to endogenous control genes (FIG. 8). This TLDA configuration allows analyzing a single sample per card. The table of FIG. 8 indicates the gene name and symbol, as well as the Affymetrix clone in which the differential expression of the gene was found. The name of the TaqMan Gene Expression Assay available from the Applied Biosystems selected for the TaqMan Low Density Array microfluidic card is also defined. This assay name is in turn indicating the gene region which will be amplified in the qRT-PCR. Finally one of the major transcripts which will be amplified with this assay (Ref Seq or Gene Bank mRNA) is indicated.

The PCRs were carried out in an ABI PRISM 9700 HD SDS (Applied Biosystems, Foster City, USA) according to the supplier's instructions.

A total of 60 samples were analyzed by means of 384-gene TLDA:
- 39 tumor bladder washing samples
- 15 control bladder washing samples
- 3 tumor urine samples
- 3 peripheral blood samples; this was carried out given that in the previous analysis, based on Affymetrix microarray, muscle tissue contamination had been observed in the supposedly pure bladder mucosa samples and there were signs for suspecting that in there could be contamination in the bladder fluid samples due to the immune system. Therefore, the decision was made to analyze 3 lymphocyte samples in order to be able to eliminate by comparison the genes which are highly expressed in blood (given that blood would be a constant contaminant in the bladder fluid samples from patients with bladder tumor).

5. Analysis of the 384-gene TLDA

Once all the PCRs were conducted, the threshold levels and baseline levels that were most suitable for each gene were established and the Ct (cycle threshold) or raw expression data by means of the SDS 2.1 program (Applied Biosystems).

Figure 6:
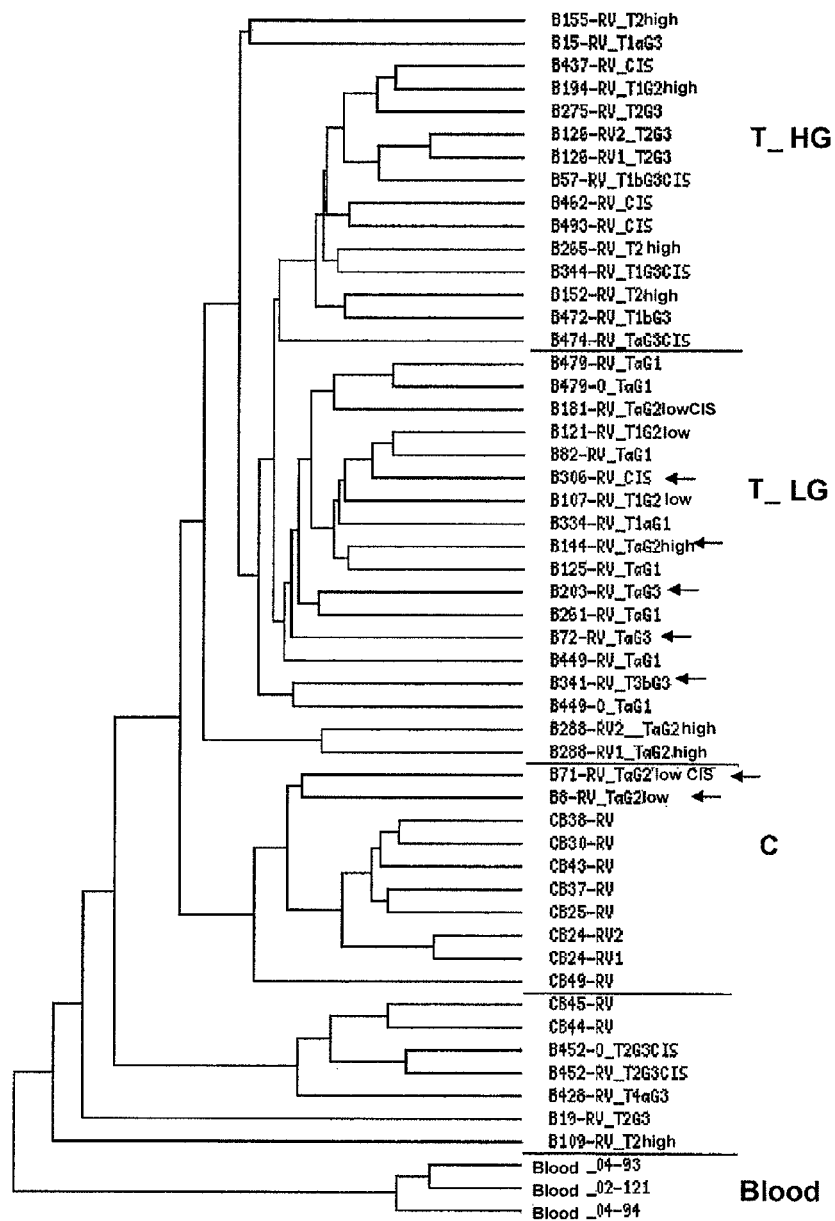
FIG. 6: Classification of the 60 individual bladder fluid samples by means of an unsupervised global cluster of 384 genes (Euclidean distance and UPGMA). The nomenclature of the samples follows the following rules: if the sample starts with the letter "B", it refers to a tumor bladder washing sample; if it starts by "CB", it refers to a control bladder fluid sample; if the initials "RV" appear after the sample number it refers to a bladder washing sample; if on the other hand, the initial "O" appears, it refers to a urine sample, and the tumor grade and pathological condition of the tumor sample is indicated after the underscore. The arrows indicate a bad classification of the sample which they indicate in relation to the established categories: T_HG (high-grade tumors); T_LG (low-grade tumors), and C (controls).

Subsequently, the relative expression measurement of each gene or delta Ct (Ct of the target gene—Ct of the endogenous control, GUSB in this case) was calculated and it was studied how the individual samples clustered together by means of an unsupervised cluster (using Euclidean distances and UPGMA) (FIG. 6). The first classification level which was observed in this cluster is the differentiation between the 3 samples from peripheral blood and the bladder fluid (bladder washings and urine) samples. In addition, the bladder fluids are sub-clustered into a group of samples which cluster together in the upper part of the cluster (from the B155-RV_T2high sample to the B288-RV1_TaG2high sample) and which is formed only by tumor bladder fluid samples, and another group of samples in the lower part of the cluster (from the B71-RV_TaG2lowCIS sample to the B109-RV_T2high sample) which is formed by a mixture of tumor and control bladder fluids. Inside the upper cluster, high-grade and low-grade tumors can in turn be distinguished, whereas in the lower cluster there is a clustering with almost only control samples and another clustering with a mixture of controls and tumors, It must be taken into account that a change has been made from analyzing tissue in pools to bladder fluids in individual samples, therefore this loss of discrimination power by means of a cluster was relatively predictable.

The objective of this analysis was to reduce the genes to be studied in the next phase, with a higher number of samples, from 384 to 96. Different parameters were taken into account for the process for selecting the best genes, including the previously described statistical parameter (minimum fold change), but also the logarithmic scale proportion of the medians of the 2 compared groups (median fold change) and an individualized manual analysis by genes of the different intensity values. This allowed reducing the initial group of 384 genes to the 96 genes required for the next phase of experiments (FIG. 9).

Example 4

Second Selection of Genes to Increase the Diagnostic/Prognostic Power

In this phase of the work, the objective was to increase the discrimination power between tumor and control samples. To that end, the intention was to analyze a higher number of bladder fluid samples and reduce, if possible, by at least half the number of genes on which the initial prototype of this diagnosis and prognosis system should be based.

1. Samples to be Analyzed and 96-gene TLDA

The microfluidic cards (TaqMan Low Density Arrays) containing 96 assays (FIG. 9) were configured and processed in the same manner as with those of 384 genes, with the difference that this TLDA configuration allows analyzing 4 samples per card.

A total of 80 samples were analyzed by means of 96 gene-TLDA:

42 tumor bladder washing samples
    8 control bladder washing samples
    15 tumor urine samples
    15 control urine samples 2. Analysis of the 96-gene TLDA Given that the technology used in the previous phase of experiments (Example 3) was exactly the same as in this example and the genes analyzed in this phase were already included in the previously analyzed 384-gene TLDA, the decision was made to extract and add the 60 samples of Example 3, with the data of the new 80 samples (Total=140 samples).

Figure 7A:
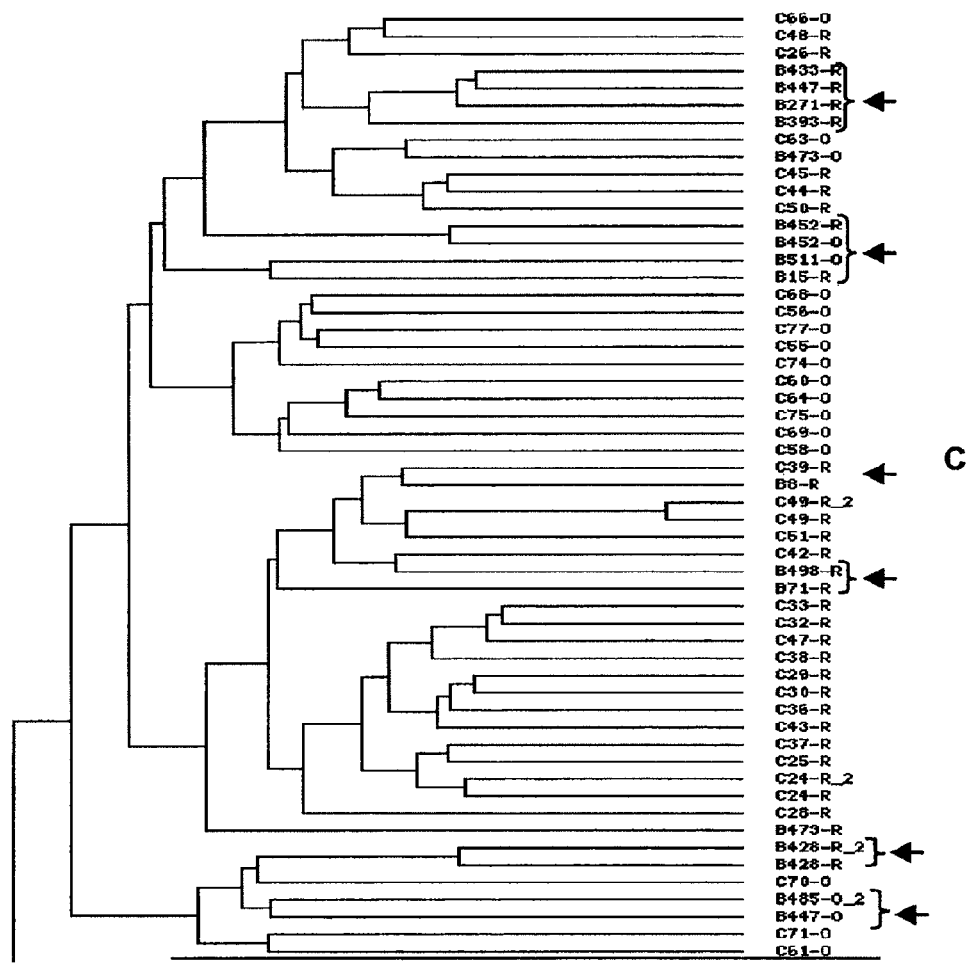
FIGS. 7 (A and B): Classification of the 140 individual bladder fluid samples by means of an unsupervised global cluster of 96 genes (Euclidean distance and UPGMA). The arrows indicate a bad classification of the sample which they indicate in relation to the established categories (C, controls.
Figure 7B:
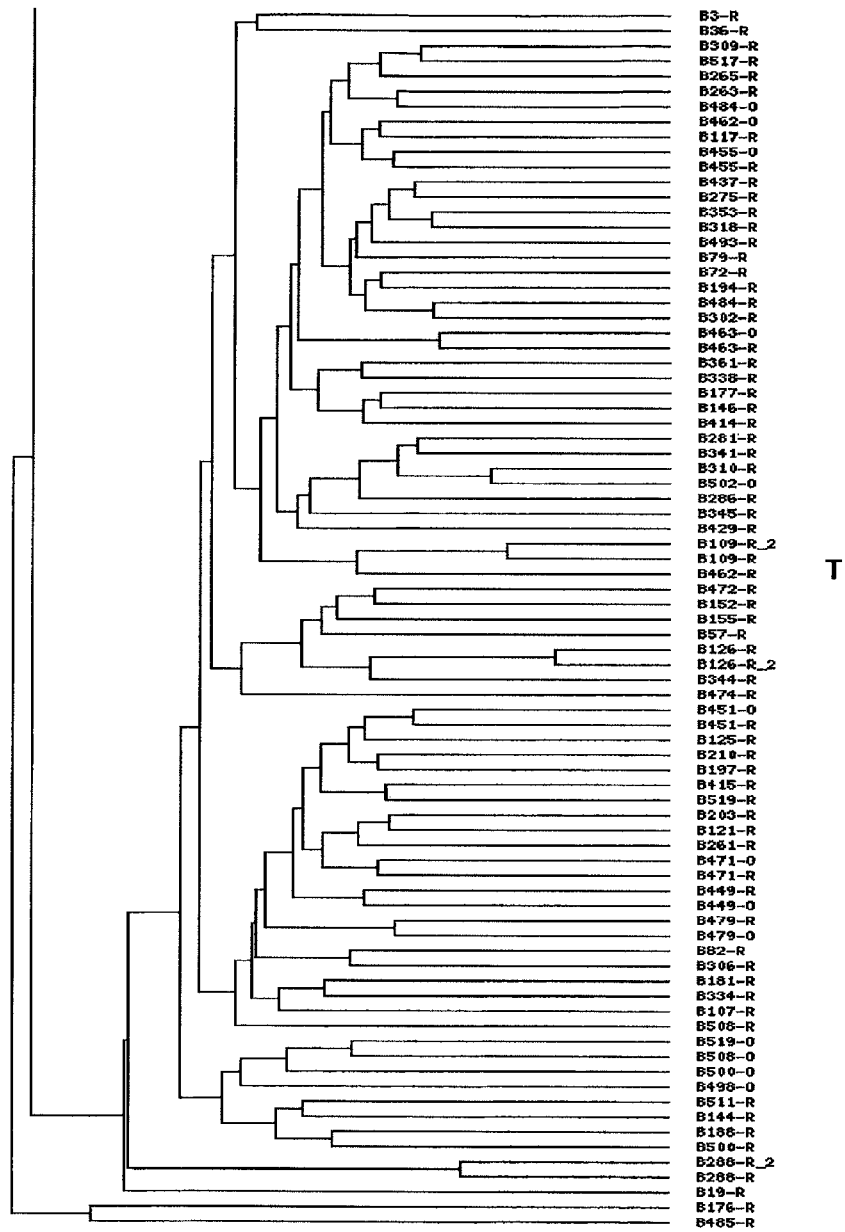

A first analysis was conducted by means of an unsupervised cluster of the 140 samples with the expressions of the 96 genes and 2 clearly distinguished large groups (FIG. 7) could be observed. In the first group (FIG. 7.B), all the samples are tumor samples without exception. In contrast, in the second group (FIG. 7.A), most of the samples are controls, but there are some tumor sample, with a genetic profile that cannot be distinguished from normal sample, The conclusion which could be extracted from this result is that most tumors had characteristic genetic profiles that were differentiated from the control samples, although there were some cases in which the general profile was not distinguished from a normal sample and, therefore, they could not be detected. The same effect as for Example 3 was being observed, although the discrimination capacity in the samples was now higher.

Based on the data observed from the clusters and in proper exploratory analyses attempting to use other classification algorithms (such as discriminating linear analysis, k-nearest neighbor (KNN), etc.), it could be observed that the problem of the discrimination of some tumors in relation to control samples persisted. The new working hypothesis was that any system for the global calculation of a discriminating measurement using a specific group of genes had the same problem, This consisted of the fact that, due to the high heterogeneity of the tumors, it was relatively easy to recognize the profiles of most of them, which would have mostly similar alterations, although there would always be a minority of cases for which the global behavior of the genes selected for their analysis would not be distinguished from the control samples, because they would have altered minority pathways.

To detect both majority and minority tumors, an "alarm system" was established by means of establishing a range of values between which the control samples ranged and adding a confidence interval such that a point could be determined from which an expression that was higher (or lower in the case of underexpressed genes) would indicate a tumor, regardless of the expression values observed in the other genes. The advantage of this system is that, although the tumor has general expression profiles similar to healthy samples, if one of the alarm genes is triggered, it allows affirming that the sample is a tumor sample.

The first step in the development of said system was the estimation of the expression ranges of the controls and their confidence intervals. Since it was very important for the control values to not have technical errors which would falsely alter the ranges, the decision was made to eliminate the controls that did not have a minimum quality level. To calculate this quality measurement, 3 genes (GUSB, 18S and PPIA) were used, which were furthermore useful as endogenous controls (by calculating their geometric mean) for the relative quantification of all the genes. By analyzing the individual behavior of the distribution of each gene, it was not possible to verify that a sufficient fit to a normal distribution was met, therefore confidence intervals based on its variance could not be established. As an alternative, the decision was made to establish arbitrary and fixed confidence intervals with different stringency levels (the decision was made to use double, 4 times or 8 times the value of the control with expression values that were more similar to the tumors as a threshold point).

Once the threshold point for each gene was determined, all this information was summarized in a matrix with the 96 genes against the tumor samples. The values which did not exceed the threshold level were marked with 0 and those that did exceed it were marked with 1 (for every stringency level). To select the best genes (with which the intention was made to reduce the profile to at least 48), two properties were taken into account: 1) that the gene could detect a high number of tumors (searching for the one having a higher sum of values 1) and 2) that this detection were as independent as possible from other alarm genes (in order to be able to detect the maximum of minority pathways).

As a result, the number of interesting genes could have been reduced to less than 48, although for technical reasons and being conservative, the decision was made to maintain this number for their analysis in subsequent phases, because some intervals in the controls might not be completely correct (due to the low number of control samples analyzed up until now).

To automate the process for analyzing new samples from the genetic profile of the 48 selected genes (FIG. 10), a computer program was created which, starting from the Cts results obtained from the qRT-PCR, can carry out a diagnostic prediction. This program can use different parameter files (depending on the stringency in the intervals), therefore the sensitivity (SN) and specificity (SP) values vary. Using the least stringent parameter file (the threshold point being double the control that is closest to the tumors), SN=100% and SP=100% was obtained. In the case of the second parameter file (the threshold point being 4 times the control that is closest to the tumors), SN=98.96% and SP=100% was obtained. In the last case (the threshold point being 8 times the worst control), SN=97.93% and SP=100% was obtained. It is important to indicate that these results have been obtained on the same samples used to generate the parameter files, therefore an overfitting is probably occurring which it would be necessary to estimate in subsequent experiments with new samples.

Example 5

Development of a Final Diagnosis Model

The objectives in this phase of the project were to test and improve the tumor prediction model as well as to reduce to a minimum the number of genes used to carry out the prediction.

For this phase, it was necessary to amplify much more the group of tumor and control samples. 440 new samples were analyzed by means microfluidic cards with 48 genes, which have been added to the data of Example 3 (60 samples) and of Example 4 (80 samples).

Once the minimum quality controls in the samples have been carried out, they were analyzed by means of the previously described qualitative alarm model. The result obtained (SN=0.81 and SP=0.81) was rather different from that obtained with the final model of Example 4, therefore the decision was made to attempt improving it, because it probably had much overtraining.

From the observation of the discretized frequency histograms of each of the genes, it could be observed how the tumor and control samples were distributed. Due to the fact of having greatly increased the sampling, the overlapping limit between the distributions has been considerably reduced. It could also be observed that, although in a very low frequency, some control cases had expression levels that were very similar to the tumors.

Although at a conceptual level, the developed qualitative alarm system was still considered a good approximation to the cell behavior of the gene expressions, the impossibility to quantify the importance of each of the genes represented a serious limitation to the predictive power thereof.

Based on the same alarm concept, the decision was made to attempt developing a quantitative model, which was possible by using Bayes' conditional probability theorem.

Since the number of analyzed samples is sufficiently high, the probabilities that, given an expression value, the sample is either a tumor or a control can be estimated from the expression frequencies observed.

One of the advantages of a model based on Bayes' theorem is that it can be independently applied to each sensor gene. The gene expression observed will modify the a priori probability of being a tumor, giving an a posteriori probability, which can be used again as an a priori probability for the next gene. In fact, independence between the different genes is being implicitly assumed.

The final number of samples on which it has been possible to apply the model was 308 tumors and 156 controls.

When this model was iteratively applied on the 48 genes, a significant improvement was obtained in the prediction power of the previous qualitative model (SN=0.86 and SP=0.92), although by studying the frequency histograms it could be observed that many genes seemed to not provide significant information to the final model. Therefore, the proposal was made to select the sub-group of genes sufficient and necessary to capture the maximum of diagnostic information of the samples.

There was no clear way of carrying out the selection of most interesting genes by using the quantitative model. The old qualitative model did allow selecting the most informative genes and, in turn, with a higher independence between them. The result of using the best genes detected with the qualitative model (CTSE, MAGEA3, CRH, SLC1A6, PPP1R14D, IGF2, C14orf78 and KLF9) over the new quantitative model showed an important improvement in the results (SN=0.89 and SP=0.96).

In any case, the decision was made to attempt other approximations. From the visual analysis of the frequency histograms of the 48 genes, the apparently most informative sub-group (ANXA10, CRH, IGF2, KRT20, MAGEA3, POSTN, SLC1A6 and TERT) and with histograms that were most varied between one another (expecting that this fact would indicate a higher independence between them) was selected. The result obtained also showed a significant improvement in relation to the analysis of the 48 genes (SN=0.90 and SP=0.96).

Finally, since both the sub-group of genes obtained by means of the qualitative model and the visually selected genes showed improvements in relation to the initial quantitative model, the decision was made to combine the genes of the 2 approximations (ANXA10, C14orf78, CTSE, CRH, IGF2, KLF9, KRT20, MAGEA3, POSTN, PPP1R14D, SLC1A6 and TERT). The result of the combined model was slightly better than any of them (SN=0.91 and SP=0.96).

Once the model was obtained, the decision was made to study if there was any common pattern both in the tumors and in the controls that were badly classified. In the case of the controls, a significant presence of samples with tumors in contact with the urinary system (mainly prostate, kidney and penis) could be detected. These types of samples probably have common expression patterns with bladder tumors, therefore they can confuse the prediction model. Therefore, the decision was made to eliminate from the control samples all the cases with tumors which might be in contact with the urinary system.

The number of control samples decreased from 156 to 126, there also being 308 tumor samples. An important improvement (SN=0.90 and SP=0.93) was observed by using the quantitative model with the 48 genes on this new population. In the case of the 8 most independent genes, SN=0.91 and SP=0.97 was obtained. In the sub-group with the most interesting histograms, SN=0.91 and SP=0.97 was obtained. Finally, in the combined sub-group of genes, SN=0.93 and SP=0.97 was obtained. It can generally be seen by calculating the data again with each previously selected sub-group that the power of the model had been increased by eliminating these types of controls.

As regards the study of the badly classified tumors, a significant increase in the number of cystectomies present in this group was detected. It is believed that the prior transurethral resection (TUR) which is frequency performed very close in time to radical surgery could be altering the molecular profile which was observed, since the tumor masses have been physically removed partially or completely from the epithelial walls of the bladder. Although in this study, cystectomy cases have not been eliminated since the data are not conclusive, it is recommended to not include these types of sample in the analysis of new populations.

Example 6

Development of a Final Prognosis Model

Although the most important concern was tumor prediction (diagnostic prediction), there was also an interest in classifying the different types of tumors (prognostic prediction), which is the main objective of this section. This classification could allow further personalizing the treatment in each case.

The tumor classification is currently based on the macroscopic and microscopic observation in the pathological anatomy laboratory. Their classification is decided by means of more or less standardized observations, based on the depth of the tumor and on the microscopic appearance of the cells. Recent molecular studies seem to indicate that there are actually two differential genetic profiles which mostly separate superficial type tumors and infiltrating tumors.

To carry out a prognosis classification model, the different groups of tumor groups must be correctly separated. The anatomical-pathological observations do not ensure the match with the behavior at molecular level of the samples, therefore it did not seem a good idea to derive a prognostic model only from this classification. The use of a classification system by means of an unsupervised cluster (which mostly separated the samples into 2 large groups) was chosen, in addition to taking into account the anatomical-pathological (AP) grade.

As a group of valid superficial tumor samples, it was necessary for them to cluster together according to the cluster in the group corresponding to them and according to AP, they had to be low-grade Ta, T1 tumors and without associated carcinoma in situ (cis). The infiltrating tumors had to belong to the corresponding group of the cluster and according to AP they had to be high-grade T1, T2, T3 or T4 tumors and any tumor with the presence of CIS.

In the group of samples defined as superficial tumors, 129 of the 308 tumors were classified. In the group defined as infiltrating tumors, 100 of the 308 tumors were classified. Finally, 79 tumor samples either had discrepancies between their anatomical-pathological classification and their molecular profile or were not clearly defined within the two major groups of the cluster.

The methodology used to create a model which would discriminate between superficial and infiltrating tumors is exactly the same as that used in Example 5 to obtain a diagnostic model.

When Bayes' theorem was applied using the 48 genes, a good classification was obtained (SN=0.97 and SP=0.96).

It could be observed that the genes interesting for diagnosis coincided to a great extent with prognostic genes by analyzing the frequency histograms. However, there were some genes (MCM10 and ASAM) which were not suitable for diagnosis and were suitable for prognosis, therefore these two genes were added to the 12 previously selected genes. The resulting model with 14 genes proved to work almost perfectly (SN=0.99 and SP=1.00). Table 1 includes the 14 genes, indicating the gene symbol and the name of the TaqMan Gene Expression Assay selected for the TaqMan Low Density Array microfluidic card.

TABLE 1

| Gene symbol | TaqMan Gene Expression Assay |
|---|---|
| ANXA10 | Hs00200464_m1 |
| C14orf78 | Hs00746838_s1 |
| CTSE | Hs00157213_m1 |
| CRH | Hs00174941_m1 |
| IGF2 | Hs00171254_m1 |
| KLF9 | Hs00230918_m1 |
| KRT20 | Hs00300643_m1 |
| MAGEA3 | Hs00366532_m1 |
| POSTN | Hs00170815_m1 |
| PPP1R14D | Hs00214613_m1 |
| SLC1A6 | Hs00192604_m1 |
| TERT | Hs00162669_m1 |
| ASAM | Hs00293345_m1 |
| MCM10 | Hs00218560_m1 |

The invention claimed is:

1. A bladder cancer diagnosis and/or prognosis kit, consisting of a set of probes suitable for the detection and quantification of the expression pattern of the combination of ANXA10, C14orf78, CTSE, CRH, IGF2, KLF9, KRT20, MAGEA3, POSTN, PPP1R14D, SLC1A6, TERT, ASAM and MCM10 genes.

2. A bladder cancer diagnosis and/or prognosis kit, consisting of a set of probes suitable for the detection and quantification of the expression pattern of the combination of ANXA10, CTSE, CRH, IGF2, KRT20, MAGEA3, SLC1A6, TERT and MCM10 genes.

3. A bladder cancer diagnosis kit, consisting of a set of probes suitable for the detection and quantification of the expression pattern of the combination of ANXA10, C14orf78, CTSE, CRH, IGF2, KLF9, KRT20, MAGEA3, POSTN, PPP1R14D, SLC1A6 and TERT genes.

4. A bladder cancer diagnosis kit, consisting of a set of probes suitable for the detection and quantification of the expression pattern of the combination of ANXA10, CTSE, CRH, IGF2, KRT20, MAGEA3, SLC1A6 and TERT genes.

* * * * *